United States Patent
Arlow et al.

(10) Patent No.: US 11,732,283 B2
(45) Date of Patent: *Aug. 22, 2023

(54) NUCLEIC ACID SYNTHESIS AND SEQUENCING USING TETHERED NUCLEOSIDE TRIPHOSPHATES

(71) Applicant: The Regents of the University of California, Oakland, CA (US)

(72) Inventors: Daniel Arlow, Berkeley, CA (US); Sebastian Palluk, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/571,529

(22) Filed: Jan. 9, 2022

(65) Prior Publication Data

US 2022/0205008 A1 Jun. 30, 2022

Related U.S. Application Data

(63) Continuation of application No. 16/230,438, filed on Dec. 21, 2018, now Pat. No. 11,254,961, which is a continuation of application No. PCT/US2017/039120, filed on Jun. 23, 2017.

(60) Provisional application No. 62/354,635, filed on Jun. 24, 2016.

(51) Int. Cl.
| | |
|---|---|
| *C12P 19/34* | (2006.01) |
| *C07K 19/00* | (2006.01) |
| *C12N 9/12* | (2006.01) |
| *C12Q 1/6869* | (2018.01) |
| *C12Q 1/6874* | (2018.01) |
| *C12Q 1/6876* | (2018.01) |

(52) U.S. Cl.
CPC .............. *C12P 19/34* (2013.01); *C07K 19/00* (2013.01); *C12N 9/1241* (2013.01); *C12N 9/1252* (2013.01); *C12Q 1/6869* (2013.01); *C12Q 1/6874* (2013.01); *C12Q 1/6876* (2013.01); *C07K 2319/21* (2013.01); *C07K 2319/24* (2013.01); *C12Y 207/07* (2013.01)

(58) Field of Classification Search
None
See application file for complete search history.

(56) References Cited

U.S. PATENT DOCUMENTS 11,254,961 B2 * 2/2022 Arlow .................. C12Q 1/6874

FOREIGN PATENT DOCUMENTS

| | | | | |
|---|---|---|---|---|
| WO | WO-2004092331 A2 * | 10/2004 | ........... | C12Q 1/6869 |
| WO | WO-2014142981 A1 * | 9/2014 | ............. | A61K 47/59 |
| WO | WO-2017190018 A1 * | 11/2017 | ........... | C12Q 1/6809 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Accession F6RGZ5. Jul. 27, 2011 (Year: 2011).*
Bundy et al. Bioconjugate Chem. 2010, 21, 255-263. (Year: 2010).*
McCombs et al. AAPS J. Mar. 2015; 17(2): 339-351. Published online Jan. 22, 2015. (Year: 2015).*

* cited by examiner

*Primary Examiner* — Christian L Fronda
(74) *Attorney, Agent, or Firm* — Richard Aron Osman

(57) ABSTRACT

Provided herein, among other things, is a conjugate comprising a polymerase and a nucleoside triphosphate, where the polymerase and the nucleoside triphosphate are covalently linked via a linker that comprises a cleavable linkage. A set of such conjugates, where the conjugates correspond to G, A, T (or U) and C is also provided. Methods for synthesizing a nucleic acid of a defined sequence are also provided. The conjugates can also be used for sequencing applications.

32 Claims, 14 Drawing Sheets

Specification includes a Sequence Listing.

PEG4-SPDP    5-aminoallyl-dUTP

BP-23354    5-propargylamino-dCTP

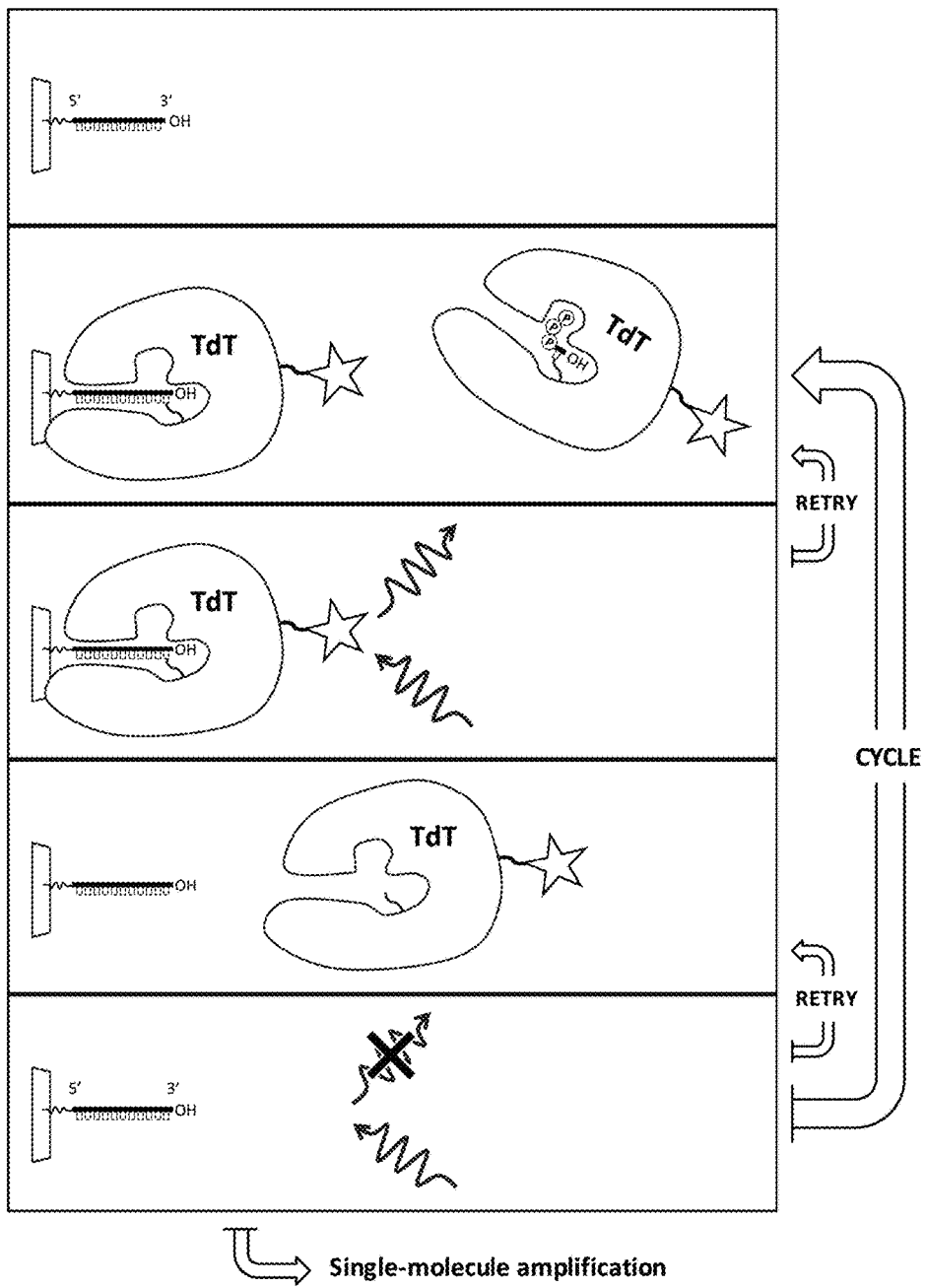
FIG. 5A Single-molecule loading
FIG. 5B Extension
FIG. 5C Extension check
FIG. 5D Deprotection
FIG. 5E Deprotection check
Single-molecule amplification Loading Template-dependent primer extension Detection Deprotection Deprotection check (optional)

CYCLE

FIG. 9A
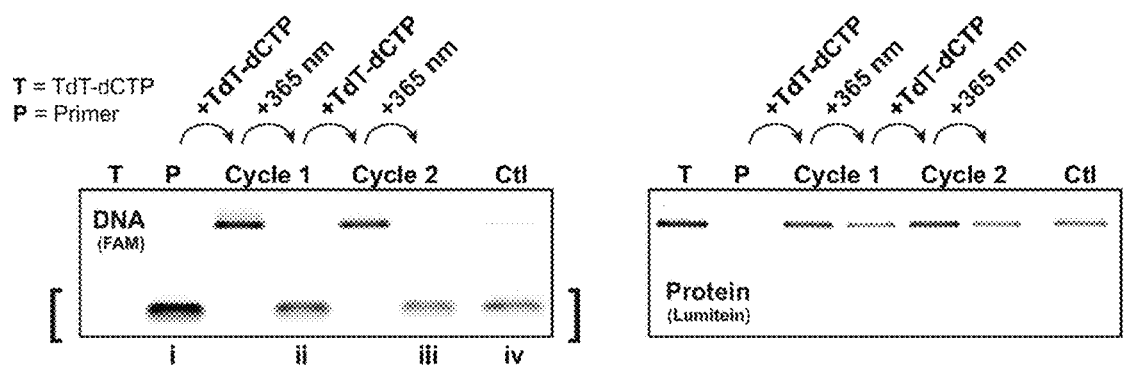
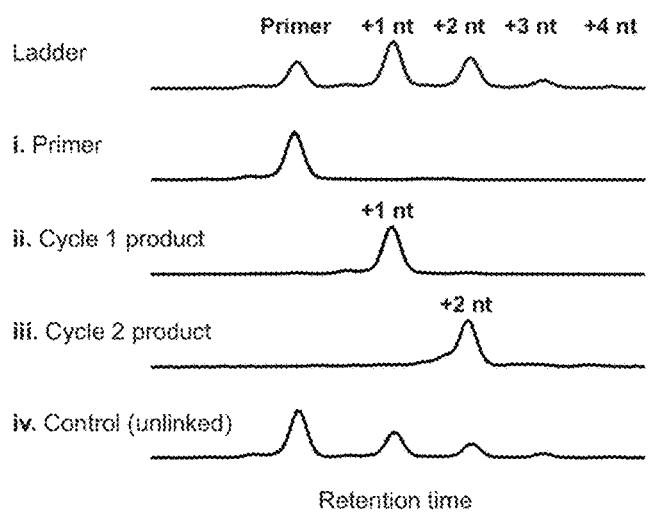
FIG. 9B

*32 clones sequenced x 10 nt = 320 attempted extensions*

| Correct extensions | Insertions | Deletions |
|---|---|---|
| 291/320 (91%) | 6/320 (2%) | 23/320 (7%) |

NUCLEIC ACID SYNTHESIS AND SEQUENCING USING TETHERED NUCLEOSIDE TRIPHOSPHATES

CROSS-REFERENCING

This application is a continuation of Ser. No. 16/230,438; filed: Dec. 21, 2018, which is a continuation of PCT/US17/39120; filed: Jun. 23, 2017, which claims the benefit of Ser. No. 62/354,635, filed on Jun. 24, 2016, which application is incorporated by reference herein.

STATEMENT OF GOVERNMENT SUPPORT

This invention was made with government support under Grant Number DE-AC02-05SC11231 awarded by the US Department of Energy. The government has certain rights in the invention.

BACKGROUND

The great majority of Next Generation Sequencing (NGS) performed today is based on "sequencing by synthesis" (SBS), in which the sequence of a primed template molecule is determined by a signal resulting from stepwise incorporation of complementary nucleotides by a polymerase (Goodwin et al., Nat Rev Genet. 2016 May 17; 17(6):333-51). Currently, the most popular method for SBS employs fluorescent "reversible terminator" nucleotides (RTdNTPs)—nucleotides that are chemically modified to block elongation by a polymerase once they are incorporated into a primer. Post-incorporation, the free RTdNTPs are removed, and the identity of the added base is determined by a fluorescent signal from the incorporated nucleotide. Next, the fluorescent reporter and terminating group are removed from the incorporated nucleotide, rendering the primer non-fluorescent and ready for subsequent extension by a polymerase. By repeating this cycle of template-dependent extension, detection, and deprotection, the sequence of the template molecule is inferred from the sequence of fluorescence signals.

Contemporary DNA synthesis begins with chemical synthesis of tens to hundreds of 50-200 nt oligonucleotides (oligos) using the phosphoramidite method (Beaucage and Caruthers, Tetrahedron Letters 22.20 (1981): 1859-1862). These oligos are assembled into kilobase-sized products that are then isolated, sequence-verified, and amplified for subsequent recombination into the full-length target sequence if necessary (Kosuri and Church, Nature methods 11.5 (2014): 499-507.). Despite decades of incremental improvement, each chemical step of oligonucleotide synthesis results in 0.5-1.0% unreacted (or side-reacted) products, and these small losses compound exponentially to decimate the yield of the full-length oligo. Since many oligos are assembled into each kilobase-sized product, the presence of even a small fraction of erroneous oligos in the assembly reaction will result in most products containing at least one error. State of the art gene synthesis techniques apply various "error correction" strategies to enrich for error-free oligos or assembly products, but erroneous oligos are reported to be "the most crucial factor in DNA synthesis protocols today" (Czar et al., Trends in biotechnology 27.2 (2009): 63-72). Furthermore, many biologically relevant sequences, such as those with repetitive or structure-forming regions and/or high or low G/C content are difficult if not impossible to construct via assembly of oligonucleotides, impeding their use in research and engineering. Thus far, there is no practical method for de novo DNA synthesis using a polymerase to extend a nucleic acid in a cyclic manner analogous to SBS.

Arguably the key advances that lead to the NGS revolution came from the development of reversible terminator deoxynucleoside triphosphates (RTdNTPs) that can be incorporated into DNA by a polymerase and reversibly terminate further dNTP addition. Improved systems enabling single nucleotide extensions of a growing nucleic acid could benefit SBS and enable practical enzymatic de novo DNA synthesis.

SUMMARY

Provided herein, among other things, is a conjugate comprising a polymerase and a nucleoside triphosphate, where the polymerase and the nucleoside triphosphate are covalently linked via a linker that comprises a cleavable linkage. A set of such conjugates, where the conjugates correspond to G, A, T (or U) and C is also provided. Methods for synthesizing a nucleic acid of a defined sequence are also provided. The conjugates can also be used for sequencing applications.

BRIEF DESCRIPTION OF THE FIGURES

The skilled artisan will understand that the drawings, described below, are for illustration purposes only. The drawings are not intended to limit the scope of the present teachings in any way.

FIG. 3A. Starting materials to produce the thiol-reactive linker-nucleotide OPSS-PEG4-amino-allyl-dUTP.

FIG. 3B. Structure of the thiol-reactive linker-nucleotide OPSS-PEG4-amino-allyl-dUTP.

FIG. 3C. Polymerase-nucleotide conjugate prepared by labeling TdT with OPSS-PEG4-amino-allyl-dUTP.

FIG. 3D. Elongation of a DNA molecule by the polymerase-nucleotide conjugate.

FIG. 3E. Cleavage of the linkage between the elongated DNA molecule and TdT.

FIG. 4A. Starting materials to produce the thiol-reactive linker-nucleotide BP-23354-propargylamino-dCTP.

FIG. 4B. Structure of the thiol-reactive, light cleavable linker-nucleotide BP-23354-propargylamino-dCTP.

FIG. 4C. Polymerase-nucleotide conjugate prepared by labeling TdT with BP-23354-propargylamino-dCTP.

FIG. 4D. Elongation of a DNA molecule by the polymerase-nucleotide conjugate.

FIG. 4E. Cleavage of the linkage between the elongated DNA molecule and TdT.

FIGS. 5A-5E. Scheme for DNA synthesis with real-time error correction using fluorescent polymerase-nucleotide conjugates.

FIG. 5A. A reaction chamber is loaded with a single molecule of the primer.

FIG. 5B. The primer is elongated by a conjugate.

FIG. 5C. The elongation reaction is confirmed by detection of the reporter moiety of the conjugate. If the reporter is not detected, the elongation reaction is repeated.

FIG. 5D. The primer is deprotected by cleavage of the linker, releasing the polymerase and reporter.

FIG. 5E. The deprotection reaction is confirmed by lack of detection of the reporter moiety. If the reporter is not detected, the deprotection reaction is repeated.

FIG. 7A. A reaction chamber is loaded with a primer-template duplex.

FIG. 7B. The primer-template duplex is exposed to a mixture of conjugates of the four nucleotides labeled by distinct fluorophores and is elongated by a conjugate complementary to the first template base to be sequenced.

FIG. 7C. The template base is identified by detection of the reporter moiety of the conjugate.

FIG. 7D. The primer is deprotected by cleavage of the linker, releasing the polymerase and reporter.

FIG. 7E. The deprotection reaction is optionally confirmed by lack of detection of the reporter moiety.

FIG. 8A. Elongation of the primer by wild-type TdT (with up to five tethered nucleotides) and a TdT mutant with only one tethered nucleotide.

FIG. 8B. Elongation of a primer by conjugates of TdT mutants with various attachment points for the tethered nucleotide.

FIGS. 9A-9B. Demonstration of the DNA synthesis reaction cycle by SDS-PAGE and capillary electrophoresis (CE).

FIG. 9A. SDS-PAGE analysis of protein-DNA complex formation and dissociation upon elongation of a primer by a polymerase-nucleotide conjugate and cleavage of the linker.

FIG. 9B. Capillary electropherograms of reaction products from FIG. 9A.

FIG. 11A. Procedure for synthesis and sequence-verification of extension products. Step 2: SEQ ID NO:15, Step 3: Top to bottom: SEQ ID NO:16, SEQ ID NO:23.

FIG. 11B. Sequencing electropherogram of one of the clones (SEQ ID NO:17).

FIG. 13A. Scheme for synthesizing a polynucleotide consisting of nucleotides with a 3-acetamidopropynyl modification ("scars").

FIG. 13B. Capillary electrophoresis analysis of the synthesized "scarred" polynucleotide.

FIG. 13C. qPCR amplification of the "scarred" polynucleotide.

FIG. 14A. Procedure for synthesis and sequence-verification of extension products. Step 1: SEQ ID NO: 19, Step 2: SEQ ID NO: 20, Step 3: Top to bottom: SEQ ID NO: 21, SEQ ID NO: 24.

FIG. 14B. Sequencing electropherogram of one of the clones (SEQ ID NO: 22) and analysis of the synthesis steps.

DETAILED DESCRIPTION

Figure 3A:
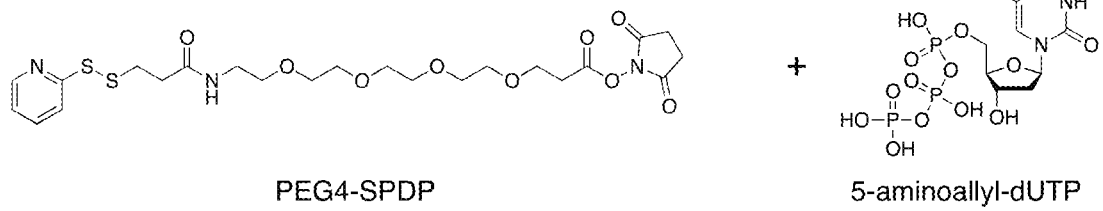
FIGS. 3A-3E. Chemical detail of a scheme for tethering dUTP to TdT and use of the conjugate to elongate a nucleic acid.
Figure 3B:
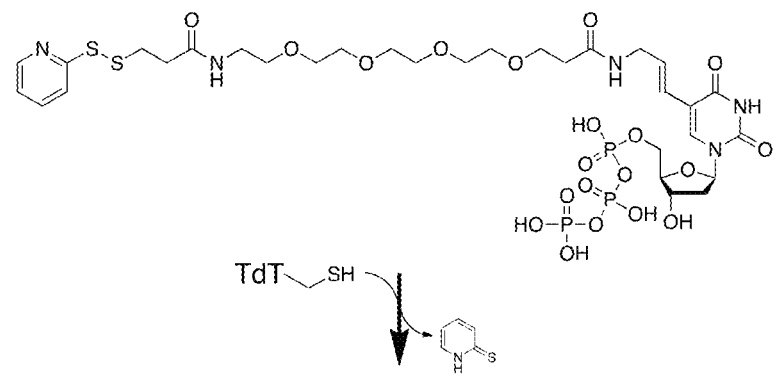
Figure 3C:
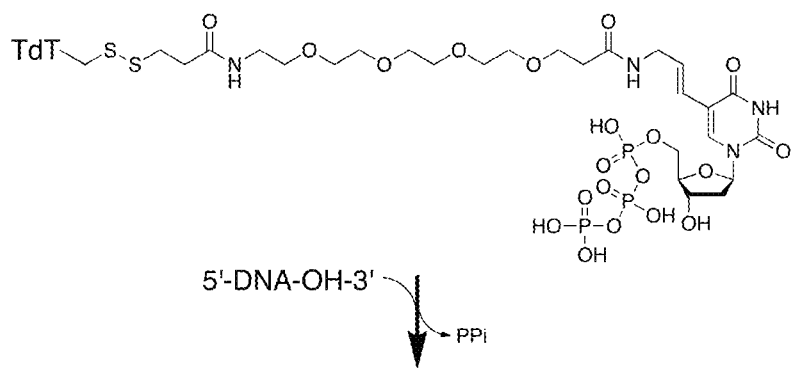
Figure 3D:
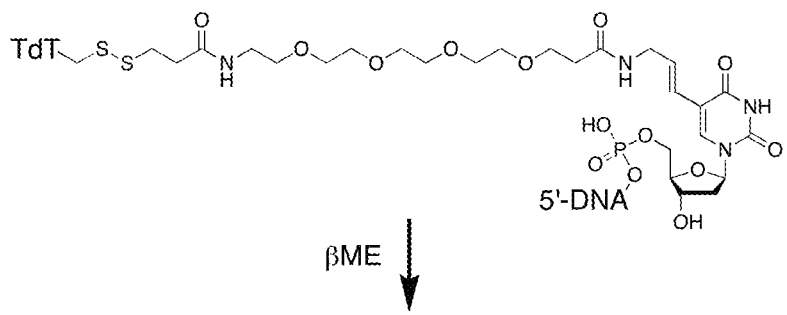
Figure 4A:
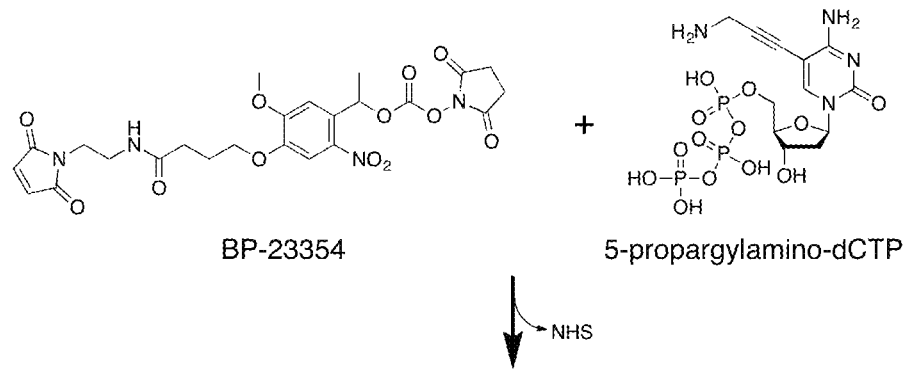
FIGS. 4A-4E. Chemical detail of a scheme for tethering dCTP to TdT based on a light cleavable linker and use of the conjugate to elongate a nucleic acid.
Figure 4B:
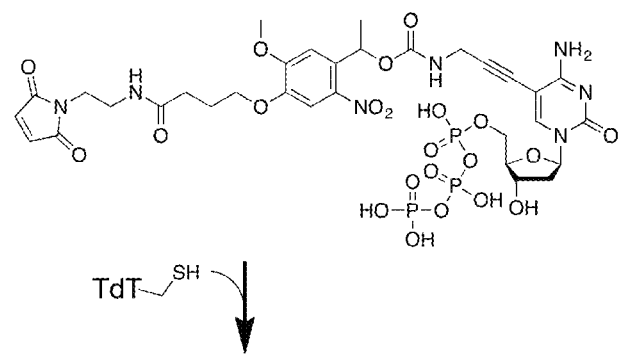
Figure 4C:
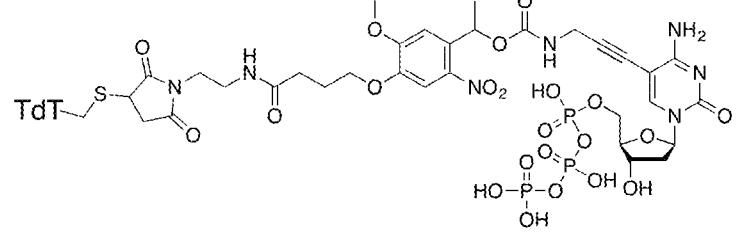

Provided herein is a conjugate comprising a polymerase and a nucleoside triphosphate, wherein the polymerase and the nucleoside triphosphate are linked via a linker that comprises a cleavable linkage. An example of such a conjugate is shown in FIG. 3C and FIG. 4C. The polymerase moiety of a conjugate can elongate a nucleic acid using its linked nucleoside triphosphate (i.e., the polymerase can catalyze the attachment of a nucleotide to which it is joined onto a nucleic acid) and remains attached to the elongated nucleic acid via the linker until the linker is cleaved.

In some embodiments, once the polymerase of a conjugate has incorporated its tethered nucleotide into a nucleic acid, further elongations of that nucleic acid by other polymerase-nucleotide conjugates are hindered via an effect referred to herein as "shielding", where the term "shielding" refers to a phenomenon in which 1) the attached polymerase molecule hinders other conjugate molecules from accessing the 3' OH of the elongated DNA molecule and 2), the nucleoside triphosphate molecules tethered to other conjugate molecules are hindered from accessing the catalytic site of the polymerase that has become attached to the end of the elongated nucleic acid. In some embodiments, further elongation of the nucleic acid may be terminated without the need for additional blocking groups on the tethered nucleoside triphosphate. The termination of elongation caused by the shielding effect may be reversed by cleavage of the linker, which releases the tethered polymerase and thereby reveals the 3' end of the elongated nucleic acid to enable subsequent elongation by another conjugate.

In any embodiment, conjugates may comprise additional moieties that contribute to termination of elongation of a nucleic acid once the tethered nucleotide has been incorporated. For example, 3' O-modified or base-modified reversible terminator deoxynucleoside triphosphates (RTdNTPs) that are well known and reviewed in a variety of publications, including Chen, Fei, et al. (Genomics, proteomics & bioinformatics 11.1 (2013): 34-40.), may be tethered to the polymerase. Reversible terminator nucleotide refers to a chemically modified nucleoside triphosphate analog that can be incubated in solution with a polymerase and a nucleic acid and, once incorporated into a nucleic acid molecule, hinders further elongation in the reaction. When a conjugate comprising a polymerase and an RTdNTP is used for the extension of a nucleic acid, besides cleavage of the linker, also deprotection of the RTdNTP may be required to enable an extended nucleic acid to undergo further nucleotide addition.

In some embodiments, the conjugate may be fluorescent, which may be useful in sequencing applications. In some embodiments, the nucleoside triphosphate may be linked to a cysteine residue in the polymerase. However, other chemistries may be used to link proteins and nucleoside triphosphate and, as such, in some cases, the nucleoside triphosphate may be linked to a non-cysteine residue in the polymerase.

The cleavable linker should be capable of being selectively cleaved using a stimulus (e.g., light, a change in its environment or exposure to a chemical or enzyme) without breakage of other bonds in the nucleic acid. In some embodiments, the cleavable linkage may be a disulfide bond, which can be readily broken using a reducing agent (e.g., β-mercaptoethanol or the like). Cleavable bonds that may be suitable may include, but are not limited to, the following: base-cleavable sites such as esters, particularly succinates (cleavable by, for example, ammonia or trimethylamine), quaternary ammonium salts (cleavable by, for example, diisopropylamine) and urethanes (cleavable by aqueous sodium hydroxide); acid-cleavable sites such as benzyl alcohol derivatives (cleavable using trifluoroacetic acid), teicoplanin aglycone (cleavable by trifluoroacetic acid followed by base), acetals and thioacetals (also cleavable by trifluoroacetic acid), thioethers (cleavable, for example, by HF or cresol) and sulfonyls (cleavable by trifluoromethane sulfonic acid, trifluoroacetic acid, thioanisole, or the like); nucleophile-cleavable sites such as phthalamide (cleavable by substituted hydrazines), esters (cleavable by, for example, aluminum trichloride); and Weinreb amide (cleavable by lithium aluminum hydride); and other types of chemically cleavable sites, including phosphorothioate (cleavable by silver or mercuric ions), diisopropyldialkoxysilyl (cleavable by fluoride ions), diols (cleavable by sodium periodate), and azobenzenes (cleavable by sodium dithionite). Other cleavable bonds will be apparent to those skilled in the art or are described in the pertinent literature and texts (e.g., Brown (1997) Contemporary Organic Synthesis 4(3); 216-237).

In particular embodiments, a photocleavable ("PC") linker (e.g., a uv-cleavable linker) may be employed. Suitable photocleavable linkers for use may include ortho-nitrobenzyl-based linkers, phenacyl linkers, alkoxybenzoin linkers, chromium arene complex linkers, NpSSMpact linkers and pivaloylglycol linkers, as described in Guillier et al (Chem Rev. 2000 Jun. 14; 100(6):2091-158). Exemplary linking groups that may be employed in the subject methods may be described in Guillier et al, supra and Olejnik et al (Methods in Enzymology 1998 291:135-154), and further described in U.S. Pat. No. 6,027,890; Olejnik et al (Proc. Natl. Acad Sci, 92:7590-94); Ogata et al. (Anal. Chem. 2002 74:4702-4708); Bai et al (Nucl. Acids Res. 2004 32:535-541); Zhao et al (Anal. Chem. 2002 74:4259-4268); and Sanford et al (Chem Mater. 1998 10:1510-20), and are purchasable from Ambergen (Boston, Mass.; NHS-PC-LC-Biotin), Link Technologies (Bellshill, Scotland), Fisher Scientific (Pittsburgh, Pa.) and Calbiochem-Novabiochem Corp. (La Jolla, Calif.).

In other embodiments, the linkage may be cleaved by an enzyme. For example, an amide linkage may be cleaved by a protease, an ester linkage may be cleaved by an esterase, and a glycosidic linkage may be cleaved by a glycosylase. In some embodiments, the cleavage reagent may also break bonds in the attached polymerase, e.g. a protease may also digest the polymerase.

Figure 4D:
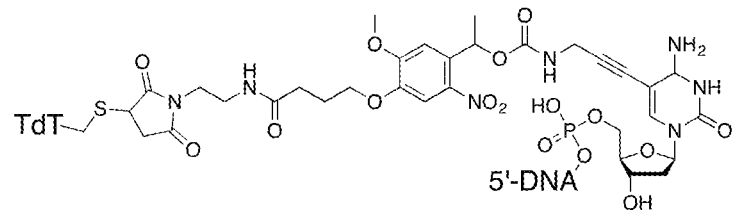

In a conjugate, the linker is considered to be at least the atoms that connect the base, the sugar, or the α-phosphate of a nucleotide to a $C_\alpha$ atom in the backbone of the polymerase. In some embodiments, the polymerase and the nucleotide are covalently linked and the distance between the linked atom of the nucleotide and the $C_\alpha$ atom in the backbone of the polymerase to which it is attached may be in the range of 4-100 Å, e.g., 15-40 or 20-30 Å, although this distance may vary depending on where the nucleoside triphosphate is tethered. In some embodiments, the linker may be a PEG or polypeptide linker, although, again, there is considerable flexibility on the type of linker used. In some embodiments, the linker should be joined to the base of the nucleotide at an atom that is not involved in base pairing. In such embodiments, the linker is considered to be at least the atoms that connect a $C_\alpha$ atom in the backbone of the polymerase to any atom in the monocyclic or polycyclic ring system bonded to the 1' position of the sugar (e.g. pyrimidine or purine or 7-deazapurine or 8-aza-7-deazapurine). For example, in the conjugate depicted in FIG. 4D, the linker is joined to the carbon atom at the 5 position of the cytosine nucleobase and to the $C_\alpha$ atom of the cysteine residue of the polymerase. In other embodiments, the linker should be joined to the base of the nucleotide at an atom that is involved in base pairing. In other embodiments, the linker should be joined to the sugar or to the α-phosphate of the nucleotide.

In all embodiments, the linker used should be sufficiently long to allow the nucleoside triphosphate to access the active site of the polymerase to which it is tethered. As will be described in greater detail below, the polymerase of a conjugate is capable of catalyzing the addition of the nucleotide to which it is linked onto the 3' end of a nucleic acid.

A nucleic acid may be at least 3 nucleotides in length, at least 10 nucleotides, at least 50 nucleotides, at least 100 nucleotides, at least 500 nucleotides, at least 1,000 nucleotides or at least 5,000 nucleotides in length and can be fully single-stranded or at least partially double-stranded, e.g., hybridized to another molecule (i.e. part of a duplex) or to itself (e.g., in the form of a hairpin). In any embodiment, a nucleic acid can be an oligonucleotide, which may be at least 3 nucleotides in length, e.g., at least 10 nucleotides, at least 50 nucleotides, at least 100 nucleotides in length, at least 500 nucleotides up to 1,000 nucleotides or more in length and can be fully single-stranded or at least partially double-stranded, e.g., hybridized to another molecule (i.e. part of a duplex) or to itself (e.g., in the form of a hairpin). In some embodiments, an oligonucleotide may be hybridized to a template nucleic acid. In these embodiments, the template nucleic acid may be at least 20 nucleotides in length, e.g., at least 80 nucleotides in length, at least 150 nucleotides in length, at least 300 nucleotides in length, at least 500 nucleotides in length, at least 2000 nucleotides in length, at least 4000 nucleotides in length or at least 10,000 nucleotides. In some cases, a nucleic acid can be part of a natural DNA substrate, e.g. it may be a strand of a plasmid. If a nucleic acid is double stranded, it can have a 3' overhang.

Also provided herein is a set of the conjugates summarized above, wherein the conjugates correspond to (i.e., have a base-pairing capability that is the same as) G, A, T (or U) and C (i.e., deoxyadenosine triphosphate (dATP), deoxyguanosine triphosphate (dGTP), deoxycytidine triphosphate (dCTP), deoxythymidine triphosphate (dTTP)).

In some embodiments, these conjugates are in separate containers. In other embodiments, the conjugates may be in the same container, particularly if they are to be used for sequencing. The nucleotides used herein may contain adenine, cytosine, guanine, and thymine bases, and/or bases that base pair with a complementary nucleotide and are capable of being used as a template by a DNA or RNA polymerase, e.g., 7-deaza-7-propargylamino-adenine, 5-propargylamino-cytosine, 7-deaza-7-propargylamino-guanosine, 5-propargylamino-uridine, 7-deaza-7-hydroxymethyl-adenine, 5-hydroxymethyl-cytosine, 7-deaza-7-hydroxymethyl-guanosine, 5-hydroxymethyl-uridine, 7-deaza-adenine, 7-deaza-guanine, adenine, guanine, cytosine, thymine, uracil, 2-deaza-2-thio-guanosine, 2-thio-7-deaza-guanosine, 2-thio-adenine, 2-thio-7-deaza-adenine, isoguanine, 7-deaza-guanine, 5,6-dihydrouridine, 5,6-dihydrothymine, xanthine, 7-deaza-xanthine, hypoxanthine, 7-deaza-xanthine, 2,6 diamino-7-deaza purine, 5-methyl-cytosine, 5-propynyl-uridine, 5-propynyl-cytidine, 2-thio-thymine or 2-thio-uridine are examples of such bases, although others are known. An exemplary set of conjugates for synthesizing and/or sequencing a DNA molecule may include a DNA polymerase linked to a deoxyribonucleotide triphosphate selected from deoxyriboadenosine triphosphate (dATP), deoxyriboguanosine triphosphate (dGTP), deoxyribocytidine triphosphate (dCTP), deoxyribothymidine triphosphate (dTTP), and/or other deoxyribonucleotides that base pair in the same way as those deoxyribonucleotides. An exemplary set of conjugates for synthesizing an RNA molecule may include an RNA polymerase linked to a ribonucleotide triphosphate selected from adenosine triphosphate (ATP), guanosine triphosphate (GTP), cytidine triphosphate (dCTP), and uridine triphosphate (UTP), and/or other ribonucleotides that base pair in the same way as those ribonucleotide triphosphates.

The above described conjugates can be used in a method of nucleic acid synthesis. In some embodiments, this method may comprise: incubating a nucleic acid with a first conjugate under conditions in which the polymerase catalyzes the covalent addition of the nucleotide of the first conjugate onto the 3' hydroxyl of the nucleic acid, to make an extension product. This reaction can be performed using a nucleic acid that is attached to a solid support or that is in solution, i.e., not tethered to a solid support. After elongation of the nucleic acid by the first desired nucleotide, the method may comprise a deprotection step wherein the cleavable linkage of the linker is cleaved, thereby releasing the polymerase from the extension product. This may be done by exposing the reaction products to reducing conditions if the cleavable linkage is a disulfide bond. However, other chemistries and reagents are available for this step. In some embodiments, the nucleoside triphosphate may be a RTdNTP and the deprotection step of the method further comprises removing the blocking group (i.e., removing the terminator group) from the added nucleotide to produce the deprotected extension product. Deprotection enables subsequent extension of the nucleic acid, and thus allows these steps to be repeated cyclically to produce an extension product of defined sequence. Specifically, in some embodiments, the method may further comprise, after deprotection: incubating the deprotected extension product with a second conjugate under conditions in which polymerase catalyzes the covalent addition of the nucleotide of the second conjugate onto the 3' end of the extension product.

In some embodiments, the method may involve (a) incubating a nucleic acid with a first conjugate under conditions in which the polymerase catalyzes the covalent addition of the nucleotide of the first conjugate (i.e., a single nucleotide) onto the 3' hydroxyl of the nucleic acid, to make an extension product; (b) cleaving the cleavable linkage of the linker, thereby releasing the polymerase from the extension product and deprotecting the extension product; (c) incubating the deprotected extension product with a second conjugate of claim 1 under conditions in which the polymerase catalyzes the covalent addition of the nucleotide of the second conjugate onto the 3' end of the extension product, to make a second extension product; (d) repeating steps (b)-(c) on the second extension product multiple times (e.g., 2 to 100 or more times) to produce an extended oligonucleotide of a defined sequence. Steps (b)-(c) may be repeated as many times as necessary until an extension product of a defined sequence and length is synthesized. The end product may be 2-100 bases in length, although, in theory, the method can be used to produce products of any length, including greater than 200 bases or greater than 500 bases.

In certain embodiments, cleavage of the linker may leave a "scar" (i.e., part of the linker) on each or some of the added nucleotides. In other embodiments, cleavage of the linker does not produce a scar.

In some embodiments, scars may be further derivatized (e.g. by alkylation of thiol-containing scars using iodoacetamide) following each deprotection step. In other embodiments, all scars in the end product may be simultaneously derivatized (e.g. by acetylation of propargylamino scars using NHS acetate.)

In some embodiments, the product may be amplified, e.g., by PCR or some other method, to yield a product without scars (as demonstrated in Example 4).

A method of sequencing is also provided. These methods may comprise incubating a duplex comprising a primer and a template with a composition comprising a set of conjugates, wherein the conjugates correspond to G, A, T and C and are distinguishably labeled, e.g., fluorescently labeled; detecting which nucleotide has been added to the primer by detecting a label that is tethered to the polymerase that has added the nucleotide to the primer; deprotecting the extension product by cleaving the linker; and repeating the incubation, detection and deprotection steps to obtain the sequence of at least part of the template.

Also provided is a reagent set that can be used to make a conjugate described above. In some embodiments, this reagent set may comprise a polymerase that has been modified to contain a single cysteine on its surface; and a set of nucleoside triphosphates, wherein each of the nucleoside triphosphates is linked to a sulfhydryl-reactive group. In some embodiments, the nucleoside triphosphates correspond to G, A, T and C. As noted above, the nucleoside triphosphates may be reversible terminators. In this reagent set, the nucleoside triphosphates may comprise a linker that has a length in the range of 4-100 Å, e.g., 15-40 Å or 20-30 Å.

In any embodiment, the polymerase can be a template-independent polymerase, i.e., a terminal deoxynucleotidyl transferase or DNA nucleotidylexotransferase, which terms are used interchangeably to refer to an enzyme having activity 2.7.7.31 using the IUBMB nomenclature. A description of such enzymes can be found in Bollum, F. J. Deoxynucleotide-polymerizing enzymes of calf thymus gland. V. Homogeneous terminal deoxynucleotidyl transferase. J. Biol. Chem. 246 (1971) 909-916; Gottesman, M. E. and Canellakis, E. S. The terminal nucleotidyltransferases of calf thymus nuclei. J. Biol. Chem. 241 (1966) 4339-4352; and Krakow, J. S., Coutsogeorgopoulos, C. and Canellakis, E. S. Studies on the incorporation of deoxyribonucleic acid. Biochim Biophys. Acta 55 (1962) 639-650, among others.

Terminal transferase embodiments may be useful for DNA synthesis.

In any embodiment, the polymerase can be a template-dependent polymerase, i.e., a DNA-directed DNA polymerase (which terms are used interchangeably to refer to an enzyme having activity 2.7.7.7 using the IUBMB nomenclature), or an DNA-directed RNA polymerase. A description of such enzymes can be found in Richardson, A. Enzymatic synthesis of deoxyribonucleic acid. XIV. Further purification and properties of deoxyribonucleic acid polymerase of *Escherichia coli*. J. Biol. Chem. 239 (1964) 222-232; Schachman, A. Enzymatic synthesis of deoxyribonucleic acid. VII. Synthesis of a polymer of deoxyadenylate and deoxythymidylate. J. Biol. Chem. 235 (1960) 3242-3249; and Zimmerman, B. K. Purification and properties of deoxyribonucleic acid polymerase from *Micrococcus lysodeikticus*. J. Biol. Chem. 241 (1966) 2035-2041.

In any of the above-summarized embodiments, the nucleoside triphosphate may be a deoxyribonucleoside triphosphate or a ribonucleoside triphosphate. In some embodiments, a conjugate may comprise an RNA polymerase linked to a ribonucleoside triphosphate. In these embodiments, the nucleotide added to the nucleic acid may be a ribonucleotide. In other embodiments, a conjugate comprises an DNA polymerase linked to a deoxyribonucleoside triphosphate. In these embodiments, the nucleotide added to the nucleic acid may be a deoxyribonucleotide.

In any embodiment, the polymerase used may have an amino acid sequence that is at least 80% identical to, e.g., at least 90% or at least 95% identical to a wild type polymerase.

In some embodiments, the yield per nucleotide addition step may be at least 70%, at least 80%, at least 90%, at least 95%, at least 97%, at least 98%, or at least 99%, for example 91% or 99.5%. The yield per step of any implementation of the method may be increased by optimizing the conditions. As would be recognized, a nucleic acid manufactured by the presented method may be purified, e.g., by liquid chromatography, prior to use.

In any embodiment, the conjugate may additionally comprise additional polypeptide domains fused to the polymerase. For example, maltose binding protein may be fused to the N-terminus of Terminal deoxynucleotidyl transferase to enhance its solubility and/or to enable amylose affinity purification. In any embodiment, the nucleoside triphosphate may be a reversible terminator.

All patents and publications, including all sequences disclosed within such patents and publications, referred to herein are expressly incorporated by reference.

Further details of the reagents and methods described above may be found below. Some of this description relates to the TdT. The principle of this description can be applied to other template-independent polymerases and template-dependent polymerases, too.

Tethered Nucleotides Can Have a High Effective Concentration, Enabling Fast Incorporation Kinetics.

A tethered nucleotide will have a certain occupancy rate with the active site of the polymerase depending on the length and geometry of the linker and its attachment site on the protein. This rate can be expressed as an effective concentration (the concentration of free nucleotide that would give an equivalent occupancy rate). By varying the linker properties and attachment site, it is possible to control the effective concentration of the nucleotide, enabling high effective concentrations and therefore fast incorporations. For example, a very rough calculation suggests that the effective concentration of a dNTP tethered by a 20 Å linker will be ~50 mM, (one molecule in the volume of a sphere with 20 Å radius). In this example, one could increase the local concentration of the dNTP by shortening the linker, or decrease it by lengthening the linker.

Attachment Position of the Linker on the Polymerase

Figure 2:
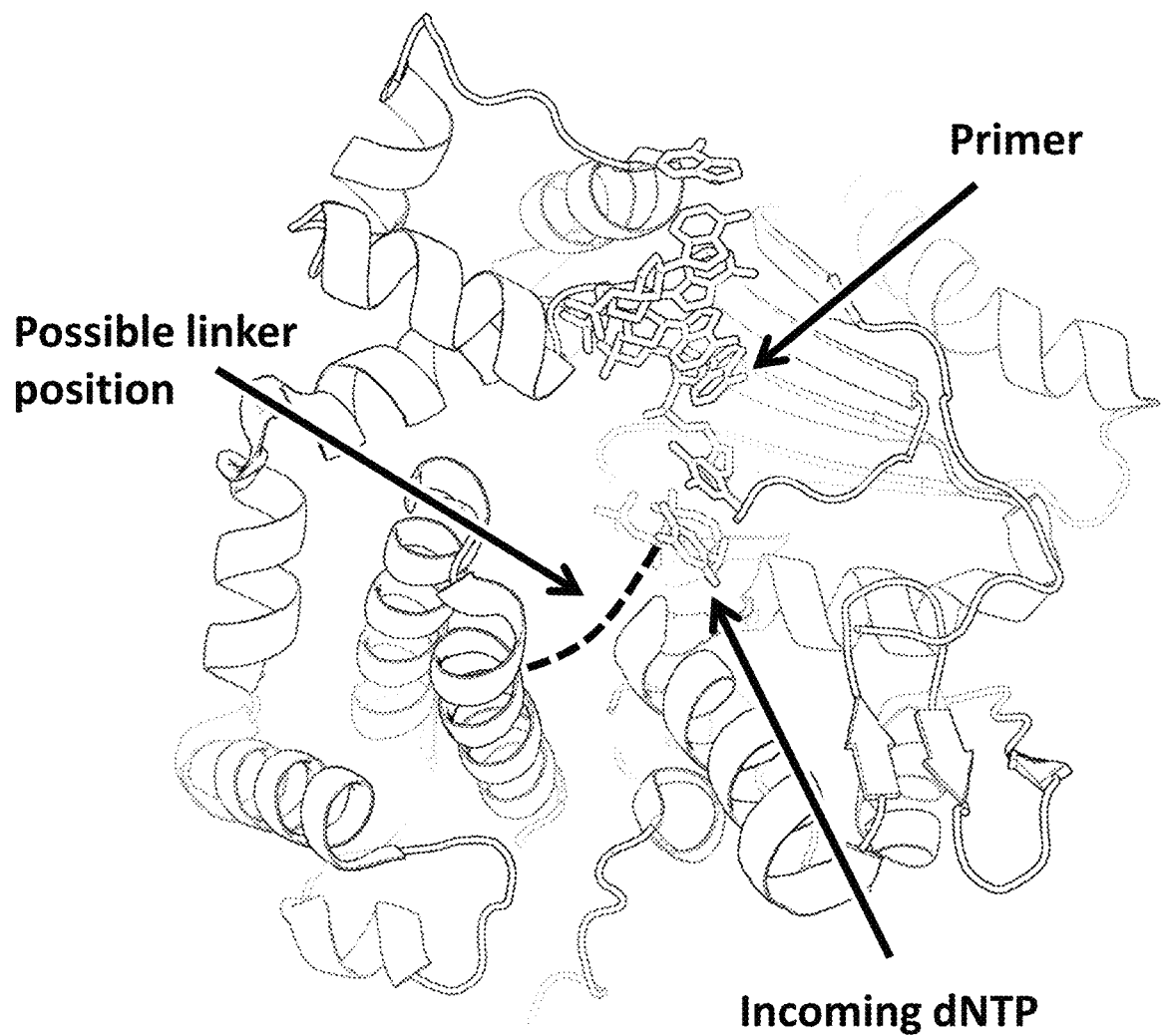
FIG. 2. Co-crystal structure of TdT (PDB ID: 4I27) with an oligonucleotide and dNTP annotated to indicate the position of a possible linker attaching the dNTP to the polymerase.

In some embodiments, the linker is specifically attached to an amino acid of the polymerase (see FIG. 2 for a schematic drawing). In these cases, it is preferable to attach the linker to an amino acid at a position that can be mutated without loss of the polymerase activity, e.g. positions 180, 188, 253 or 302 of murine TdT (numbering as in the crystal structure PDB ID: 4I27). It is preferable to not attach the linker to an amino acid involved in the catalytic activity of the polymerase to avoid interfering with catalysis. Residues known to be involved with catalysis and methods for determining if a residue is involved with catalysis (e.g. by site-specific mutagenesis) will be apparent to those skilled in the art and are reviewed in literature (e.g. Joyce et al. (Journal of Bacteriology 177.22 (1995): 6321.) and Jara and Martinez (The Journal of Physical Chemistry B 120.27 (2016): 6504-6514.))

Length of the Linker

In any embodiment, the length of the linker may be longer than the distance between the attachment position of the linker on the polymerase and the attachment position on the nucleoside triphosphate when it is bound to the catalytic site. In some cases, steric restrictions, e.g. due to the polymerase or due to the linker can restrict mobility of the tethered nucleoside triphosphate requiring an increased linker length to enable the tethered nucleoside triphosphate to access the catalytic site of the polymerase in a productive conformation. For example, the linker length may exceed the distance between its two attachment points by 2-3 Å or 5-10 Å, or 10-25 Å, or longer.

Strategies for Site-Specific Attachment of a Linker to a Polymerase.

In some embodiments, the tethered nucleoside triphosphate may be specifically attached to a cysteine residue of the polymerase using a sulfhydryl-specific attachment chemistry. Possible sulfhydryl specific attachment chemistries include, but are not limited to ortho-pyridyl disulfide (OPSS) (as exemplified in FIG. 3 and demonstrated in Example 1), maleimide functionalities (as exemplified in FIG. 4 and demonstrated in Example 2), 3-arylpropiolonitrile functionalities, allenamide functionalities, haloacetyl functionalities such as iodoacetyl or bromoacetyl, alkyl halides or perfluroaryl groups that can favorably react with sulfhydryls surrounded by a specific amino acid sequence (Zhang, Chi, et al. Nature chemistry 8, (2015) 120-128.). Other attachment chemistries for specific labeling of cysteine residues will be apparent to those skilled in the art or are described in the pertinent literature and texts (e.g., Kim, Younggyu, et al, Bioconjugate chemistry 19.3 (2008): 786-791.).

In other embodiments, the linker could be attached to a lysine residue via an amine-reactive functionality (e.g. NHS esters, Sulfo-NHS esters, tetra- or pentafluorophenyl esters, isothiocyanates, sulfonyl chlorides, etc.).

In other embodiments, the linker may be attached to the polymerase via attachment to a genetically inserted unnatural amino acid, e.g. p-propargyloxyphenylalanine or p-azidophenylalanine that could undergo azide-alkyne Huisgen cycloaddition, though many suitable unnatural amino acids suitable for site-specific labeling exist and can be found in the literature (e.g. as described in Lang and Chin., Chemical reviews 114.9 (2014): 4764-4806.).

In other embodiments, the linker may be specifically attached to the polymerase N-terminus. In some embodiments, the polymerase is mutated to have an N-terminal serine or threonine residue, which may be specifically oxidized to generate an N-terminal aldehyde for subsequent coupling to e.g. a hydrazide. In other embodiments, the polymerase is mutated to have an N-terminal cysteine residue that can be specifically labeled with an aldehyde to form a thiazolidine. In other embodiments, an N-terminal cysteine residue can be labeled with a peptide linker via Native Chemical Ligation.

In other embodiments, a peptide tag sequence may be inserted into the polymerase that can be specifically labeled with a synthetic group by an enzyme, e.g. as demonstrated in the literature using biotin ligase, transglutaminase, lipoic acid ligase, bacterial sortase and phosphopantetheinyl transferase (e.g. as described in refs. 74-78 of Stephanopoulos & Francis Nat. Chem. Biol. 7, (2011) 876-884).

In other embodiments, the linker is attached to a labeling domain fused to the polymerase. For example, a linker with a corresponding reactive moiety may be used to covalently label SNAP tags, CLIP tags, HaloTags and acyl carrier protein domains (e.g. as described in refs. 79-82 of Stephanopoulos & Francis Nat. Chem. Biol. 7, (2011) 876-884).

In other embodiments, the linker is attached to an aldehyde specifically generated within the polymerase, as described in Carrico et al. (Nat. Chem. Biol. 3, (2007) 321-322). For example, after insertion of an amino acid sequence that is recognized by the enzyme formylglycine-generating enzyme (FGE) into the polymerase, it may be exposed to FGE, which will specifically convert a cysteine residue in the recognition sequence to formylglycine (i.e. producing an aldehyde). This aldehyde may then be specifically labeled with e.g. a hydrazide or aminooxy moiety of a linker.

In some embodiments, a linker may be attached to the polymerase via non-covalent binding of a moiety of the linker to a moiety fused to the polymerase. Examples of such attachment strategies include fusing a polymerase to streptavidin that can bind a biotin moiety of a linker, or fusing a polymerase to anti-digoxigenin that can bind a digoxigenin moiety of a linker.

In some embodiments, site-specific labeling may lead to an attachment of the linker to the polymerase that may readily be reversed (e.g. an ortho-pyridyl disulfide (OPSS) group that forms a disulfide bond with a cysteine that can be cleaved using reducing agents, e.g. using TCEP), other attachment chemistries will produce permanent attachments.

In any embodiment, the polymerase may be mutated to ensure specific attachment of the tethered nucleotide to a particular location of the polymerase, as will be apparent to those skilled in the art. For example, with sulfhydryl-specific attachment chemistries such as maleimides or ortho-pyridyl disulfides, accessible cysteine residues in the wild-type polymerase may be mutated to a non-cysteine residue to prevent labeling at those positions. On this "reactive cysteine-free" background, a cysteine residue may be introduced by mutation at the desired attachment position. These mutations preferentially do not interfere with the activity of the polymerase.

Other strategies for site-specific attachment of synthetic groups to proteins will be apparent to those skilled in the art and are reviewed in literature, (e.g. Stephanopoulos & Francis Nat. Chem. Biol. 7, (2011) 876-884).

Strategies for Attaching a Linker to a Nucleoside Triphosphate.

In some embodiments, the linker is attached the 5 position of pyrimidines or the 7 position of 7-deazapurines. In other embodiments, the linker may be attached to an exocyclic amine of a nucleobase, e.g. by N-alkylating the exocyclic amine of cytosine with a nitrobenzyl moiety as discussed below. In other embodiments, the linker may be attached to any other atom in the nucleobase, sugar, or α-phosphate, as will be apparent to those skilled in the art.

Certain polymerases have a high tolerance for modification of certain parts of a nucleotide, e.g. modifications of the 5 position of pyrimidines and the 7 position of purines are well-tolerated by some polymerases (He and Seela., Nucleic Acids Research 30.24 (2002): 5485-5496.; or Hottin et al., Chemistry. 2017 Feb. 10; 23(9):2109-2118). In some embodiments, the linker is attached to these positions.

In some examples, a polymerase-nucleotide conjugate is prepared by first synthesizing an intermediate compound comprising a linker and a nucleoside triphosphate (referred to herein as a "linker-nucleotide"), and then this intermediate compound is attached to the polymerase. In some examples, nucleosides with substitutions compared to natural nucleosides, e.g. pyrimidines with 5-hydroxymethyl or 5-propargylamino substituents, or 7-deazapurines with 7-hydroxymethyl or 7-propargylamino substituents may be useful starting materials for preparing linker-nucleotides. An exemplary set of nucleosides with 5- and 7-hydroxymethyl substituents that may be useful for preparing linker-nucleotides is shown below:

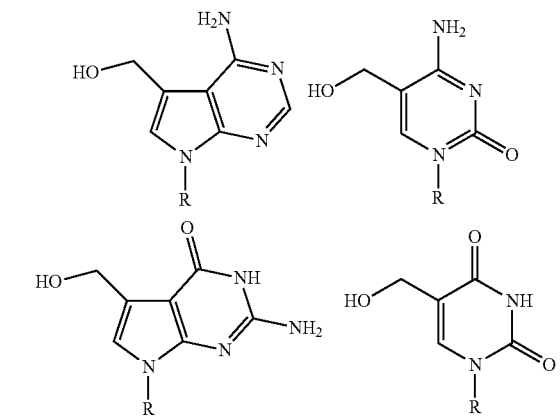

An exemplary set of nucleosides with 5- and 7-deaza-7-propargylamino substituents that may be useful for preparing linker-nucleotides is shown below:

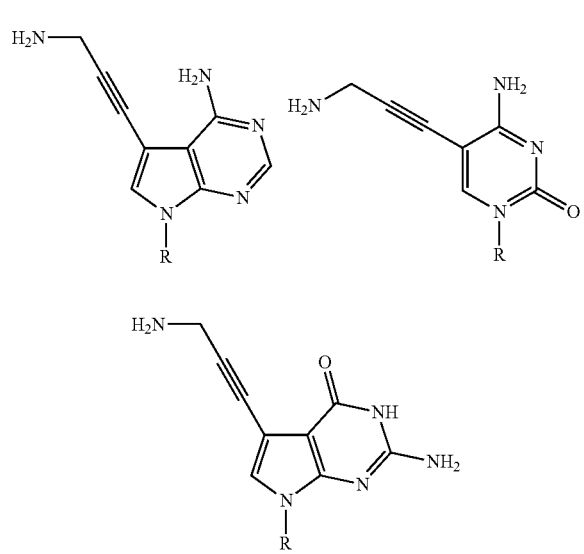

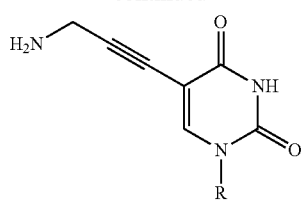

These nucleosides are also commercially available as deoxyribonucleoside triphosphates.

In Example 2, linker-nucleotides comprising a 3-(((2-nitrobenzyl)oxy)carbonyl)aminopropynyl group attached to the 5 position of pyrimidines and the 7 position of 7-deazapurines were prepared by reacting nucleoside triphosphates containing 5- and 7-propargylamino substituents with a precursor molecule comprising a nitrobenzyl NHS carbonate ester (as shown in FIG. 4).

Linker Cleavage Strategies

As described above, the linker may be attached to various positions on the nucleotide, and a variety of cleavage strategies may be used. Those strategies may include, but are not limited to, the following examples:

In some embodiments, the linker may be cleaved by exposure to a reducing agent such as dithiothreitol (DTT). For example, a linker comprising a 4-(disulfaneyl)butanoyloxy-methyl group attached to the 5 position of a pyrimidine or the 7 position of a 7-deazapurine may be cleaved by reducing agents (e.g. DTT) to produce a 4-mercaptobutanoyloxymethyl scar on the nucleobase. This scar may undergo intramolecular thiolactonization to eliminate a 2-oxothiolane, leaving a smaller hydroxymethyl scar on the nucleobase. An example of such a linker attached to the 5 position of cytosine is depicted below, but the strategy is applicable to any suitable nucleobase:

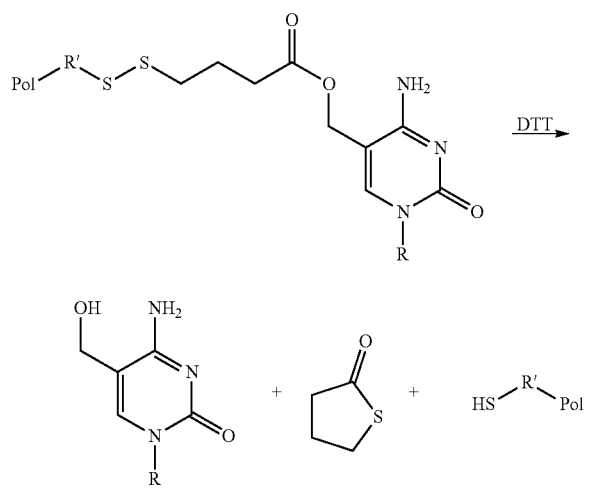

In other embodiments, the linker may be cleaved by exposure to light. For example a linker comprising (2-nitrobenzyl)oxymethyl group may be cleaved with 365 nm light, leaving a hydroxymethyl scar, e.g. as depicted for cytosine below, but as is applicable to any suitable nucleobase:

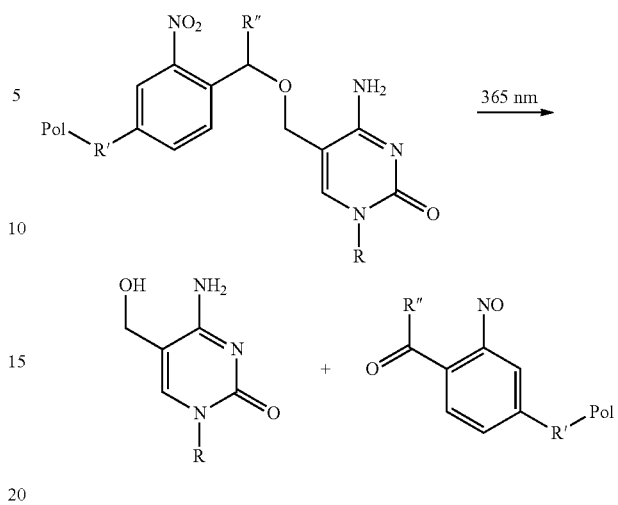

(where, e.g., R''=H or R''=CH3 or R''=t-Bu.)

In other embodiments, the linker may comprise a 3-(((2-nitrobenzyl)oxy)carbonyl)aminopropynyl group that may be cleaved with 365 nm light to release a nucleobase with a propargylamino scar. This strategy was used in Example 2 and is depicted for cytosine below, but is applicable to any suitable nucleobase:

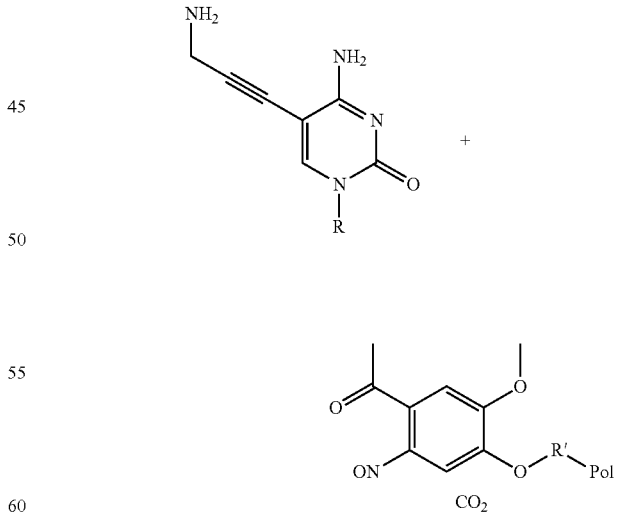

In other embodiments, the linker may comprise an acyloxymethyl group that may be cleaved with a suitable esterase to release a nucleobase with a hydroxymethyl scar, e.g. as depicted for cytosine below, but as is applicable to any suitable nucleobase:

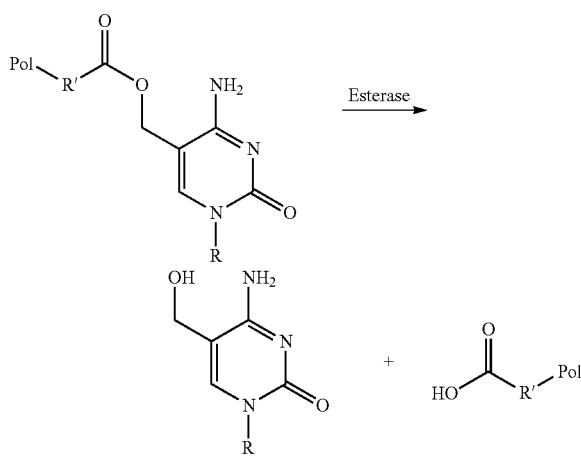

In such embodiments, the linker may comprise additional atoms (included in R' above) adjacent to the ester that increase the activity of the esterase towards the ester bond.

In other embodiments, the linker may comprise an N-acyl-aminopropynyl group that may be cleaved with a peptidase to release a nucleobase with propargylamino scar, e.g. as depicted for 5-propargylamino cytosine below, but as is applicable to any suitable nucleobase:

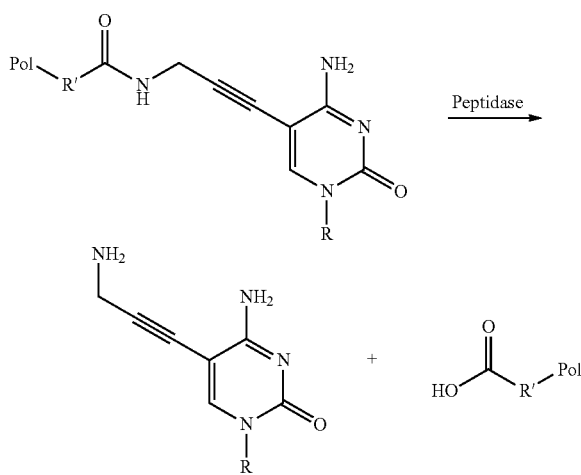

In such embodiments, the linker may comprise additional atoms (included in R' above) adjacent to the amide that increase the activity of the peptidase towards the amide bond. In some embodiments, R' is a peptide or polypeptide.

Cleavage of Peptide Bonds to Detach the Tethered Nucleotide

In some embodiments, one or more amino acids are inserted into the polymerase that can serve as part of the cleavable linker for specific attachment of the nucleotide. In this case, the linker comprises the inserted amino acids, and the cleavable linkage is considered to be one or more bonds of the inserted amino acid(s). For example, peptide bonds may be cleaved using a peptidase (which terms are used interchangeably to refer to an enzyme having activity 3.4. using the IUBMB nomenclature) such as Proteinase K (EC 3.4.21.64 using the IUBMB nomenclature).

In some embodiments, the protein itself can be cleaved to detach the tethered nucleoside triphosphate from the poly- merase. For example, peptide bonds before and/or after the attachment position of the linker may be cleaved using a peptidase.

In some embodiments, amino acid positions close to the attachment point of the linker may be mutated to ensure that peptide sequences near the attachment point are good substrates for the protease, as will be apparent to those skilled in the art. E.g., mutations into aliphatic amino acids as leucine or phenylalanine may be introduced to achieve fast cleavage with proteinase K.

RTdNTP-Polymerase Conjugates.

In certain embodiments, nucleotide analogs are tethered that, when freely available in solution, do not terminate DNA synthesis upon incorporation. However, in other embodiments nucleotide analogs containing a reversible terminator group, such as an O-azidomethyl or O—NH$_2$ group on the 3' position of the sugar or an (alpha-tertbutyl-2-nitrobenzyl)oxymethl group on the 5 position of pyrimidines or the 7 position of 7-deazapurines (for an overview see, e.g. Chen et al., Genomics, Proteomics & Bioinformatics 2013 11: 34-40.) are tethered. In these embodiments, the nucleotide analog prevents or hinders further elongation once incorporated into a nucleic acid and thus contributes to the conjugate's ability to achieve termination, possibly in addition to other properties of the conjugate that contribute to termination (e.g. shielding). In the case that RTdNTP-polymerase conjugates do not rely on the shielding effect to achieve termination, e.g. when a 3' modified RTdNTP is tethered to the polymerase, the linker used may exceed 100 Å or 200 Å in length.

Shielding Effect by Polymerase-Nucleotide Conjugates

Figure 3E:
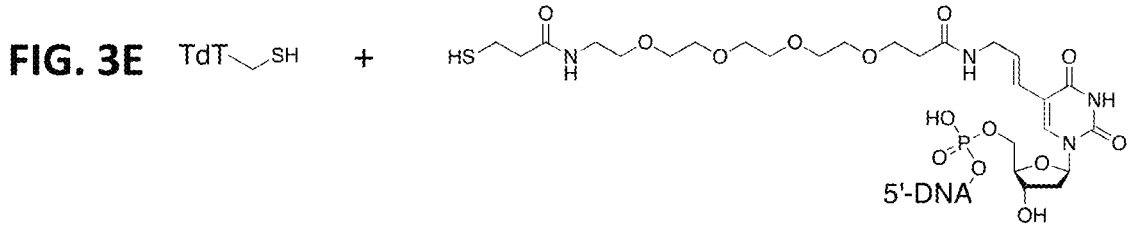
Figure 4E:
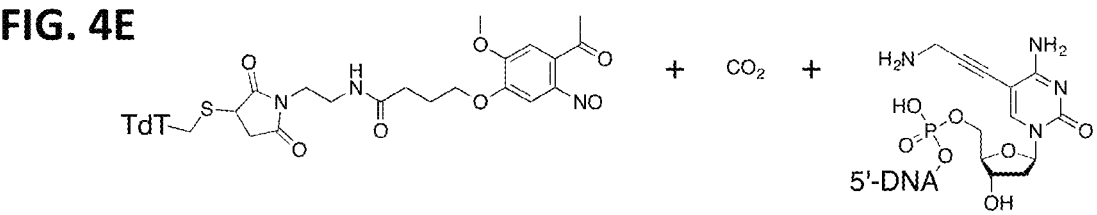

When a conjugate comprising a polymerase and a nucleoside triphosphate is incubated with a nucleic acid, it preferentially elongates the nucleic acid using its tethered nucleotide (as opposed to using the nucleotide of another conjugate molecule). As described above, the polymerase then remains attached to the nucleic acid via its tether to the added nucleotide (e.g. FIG. 3D and FIG. 4D) until exposed to some stimulus that causes cleavage of the linkage to the added nucleotide. In this situation, further extensions by polymerase-nucleotide conjugates are hindered due to "shielding" when: 1) the attached polymerase molecule hinders other conjugates from accessing the 3' OH of the extended DNA molecule and 2), other nucleoside triphosphates in the system are hindered from accessing the catalytic site of the polymerase that remains attached to the 3' end of the extended nucleic acid. (The extent of shielding may be described as the extent to which both of these interactions are hindered.) To enable subsequent extensions, the linker tethering the incorporated nucleotide to the polymerase can be cleaved, releasing the polymerase from the nucleic acid and therefore re-exposing its 3' OH group for subsequent elongation (e.g. as depicted in FIG. 3E and FIG. 4E).

Methods for nucleic acid synthesis and sequencing provided herein that employ the shielding effect to achieve termination comprise an extension step wherein a nucleic acid is exposed to conjugates preferentially in the absence of free (i.e. untethered) nucleoside triphosphates, because the termination mechanism of shielding may not prevent their incorporation into the nucleic acid. As shown in Example 3, exposing a primer that has been extended by a TdT-dCTP conjugate to free dCTP results in several additional elongations.

In some embodiments, termination of further elongation may be "complete", meaning that after a nucleic acid molecule has been elongated by a conjugate, further elongations cannot occur during the reaction. In other embodiments, termination of further elongation may be "incomplete", meaning that further elongations can occur during the reaction but at a substantially decreased rate compared to the initial elongation, e.g. 100 times slower, or 1000 times slower, or 10,000 times slower, or more. Conjugates that achieve incomplete termination may still be used to extend a nucleic acid by predominantly a single nucleotide (e.g. in methods for nucleic acid synthesis and sequencing) when the reaction is stopped after an appropriate amount of time.

In some embodiments, the reagent containing the conjugate may additionally contain polymerases without tethered nucleoside triphosphates, but those polymerases should not significantly affect the reaction because there are no free dNTPs in the mix.

Reagents based on conjugates employing the shielding effect to achieve termination preferentially only contain polymerase-nucleotide conjugates in which all polymerases remain folded in the active conformation. In some cases, if the polymerase moiety of a conjugate is unfolded, its tethered nucleoside triphosphate may become more accessible to the polymerase moieties of other conjugate molecules. In these cases, the unshielded nucleotides may be more readily incorporated by other conjugate molecules, circumventing the termination mechanism.

Polymerase-nucleotide conjugates employing the shielding effect to achieve termination are preferentially only labeled with a single nucleoside triphosphate moiety. Polymerase-nucleotide conjugates labeled with multiple nucleoside triphosphates that can access the catalytic site can, in some cases, incorporate multiple nucleoside triphosphates into the same nucleic acid (e.g. as demonstrated with the conjugate of wt TdT labeled with up to 5 nucleoside triphosphates in Example 1). Additional tethered nucleotides may therefore lead to additional, undesired nucleotide incorporations into a nucleic acid during a reaction. Furthermore, only one tethered nucleoside triphosphates can occupy the (buried) catalytic site of its polymerase at a time so the other tethered nucleoside triphosphate(s) may have an increasing accessibility to the polymerase moieties of other conjugate molecules, as discussed below. Strategies for site-specifically tethering at most one nucleoside triphosphate to a polymerase are described above.

Polymerase-nucleotide conjugates employing the shielding effect to achieve termination preferentially comprise as short of a linker as possible that still enables the nucleoside triphosphate to frequently access the catalytic site of its tethered polymerase molecule in a productive conformation, in order to enable fast incorporation of the nucleotide into a nucleic acid. Such conjugates may also preferentially employ an attachment position of the linker to the polymerase as close to the catalytic site as possible, enabling use of a shorter linker. The length of the linker will determine the maximum distance from the attachment point a tethered nucleoside triphosphate or a tethered nucleic acid can reach. A smaller distance may lead to a reduced accessibility of the tethered moiety to other polymerase-nucleotide molecules, as discussed below. Linkers used in Examples 1 and 2 are approximately 24 and 28 Å long. Shorter linkers, e.g. with lengths of 8-15 Å may increase shielding; longer linkers, e.g. linkers longer than 50 Å, 70 Å or 100 Å, may reduce shielding.

The shielding effect may be influenced by a combination of factors including, but not limited to, the structure of the polymerase, the length of the linker, the structure of the linker, the attachment position of the linker to the polymerase, the binding affinity of the nucleoside triphosphate to the catalytic site of the polymerase, the binding affinity of the nucleic acid to the polymerase, the preferred conformation of the polymerase, and the preferred conformation of the linker.

One contribution to shielding can be steric effects that block the 3' OH of a nucleic acid that has been elongated by a conjugate from reaching into the catalytic site of another conjugate's polymerase moiety. Steric effects may also hinder a tethered nucleoside triphosphate from reaching into the catalytic site of another polymerase-nucleotide conjugate molecule due to clashes between the conjugates that would occur during such approaches. These steric effects may result in complete termination if they completely block productive interactions between the tethered nucleoside triphosphate (or elongated nucleic acid) of one conjugate molecule with another conjugate molecule, or may result in incomplete termination if they only hinder such intermolecular interactions.

Another contribution to shielding arises from the binding affinity of the tethered nucleoside triphosphate to the catalytic site of the polymerase. The tethered nucleoside triphosphate of a conjugate will have a high effective concentration with respect to the catalytic site of its tethered polymerase so it may remain bound to that site much of the time. When the nucleoside triphosphate is bound to the catalytic site of its tethered polymerase molecule it is unavailable for incorporation by other polymerase molecules. Thus, tethering reduces the effective concentration of nucleoside triphosphates available for intermolecular incorporation (i.e. incorporation catalyzed by a polymerase molecule to which the nucleotide is not tethered). This shielding effect can enhance termination by reducing the rate by which a nucleic acid is elongated using the nucleoside triphosphate moiety of one conjugate molecule by the polymerase moiety of another conjugate molecule.

Another contribution to shielding arises from the binding affinity of the 3' region of a nucleic acid molecule to the catalytic site of a polymerase molecule. After elongation by a conjugate, the nucleic acid is tethered to the conjugate via it's 3' terminal nucleotide and will have a high effective concentration with respect to the catalytic site of its tethered polymerase so it may remain bound to that site much of the time. When the nucleic acid is bound to the catalytic site of its tethered polymerase molecule it is unavailable for elongation by other conjugate molecules. This effect can enhance termination by reducing the rate by which a nucleic acid that has been elongated by a first conjugate is further elongated by other conjugate molecules.

Addition of Elements with Steric Restrictions to Increase the Shielding Effect

In some embodiments, the polymerase-nucleotide conjugates comprise additional moieties that sterically hinder the tethered nucleoside triphosphate (or a tethered nucleic acid post-elongation) from approaching the catalytic sites of another conjugate molecule. Such moieties include polypeptides or protein domains that can be inserted into a loop of the polymerase, and those and other bulky molecules such as polymers that can be site-specifically ligated e.g. to an inserted unnatural amino acid or specific polypeptide tag.

RTdNTP Termination Mechanisms in Combination with the Shielding Effect.

As described above, in some embodiments, a conjugate may comprise a polymerase and a tethered reversible terminator nucleoside triphosphate. Some RTdNTPs (particularly 3' O-unblocked RTdNTPs) achieve incomplete termination when used freely in solution. A polymerase-nucleotide conjugate of such an RTdNTP that also employs a shielding effect may achieve more complete termination than the RTdNTP used by itself. In some embodiments, an RTdNTP with an (alpha-tertbutyl-2-nitrobenzyl)oxymethyl group attached to the 5 position of a pyrimidine or the 7 position of a 7-deazapurine in a nucleoside triphosphate e.g. described in Gardner et al. (Nucleic Acids Res. 2012 August; 40(15):7404-1); or Stupi et al. (Angewandte Chemie International Edition 51.7 (2012): 1724-1727) may be employed. In some embodiments, the linker is attached to an atom in the terminating moiety of the RTdNTP. In other embodiments the linker is attached to an atom of the RTdNTP not in the terminating moiety.

Effective Concentration of Nucleoside Triphosphates Tethered to Other Polymerase-Nucleotide Conjugates As described earlier, a tethered nucleoside triphosphate has a high effective concentration with respect to the catalytic site of its attached polymerase moiety, enabling fast incorporation. The same nucleoside triphosphate has a much lower concentration with respect to the catalytic site of other polymerase-moieties, leading to a slower intermolecular nucleotide incorporation rate if intermolecular incorporations are possible. The effective concentration of nucleoside triphosphates tethered to other conjugates is at most the absolute concentration of conjugates since each conjugate molecule comprises a single nucleotide. Due to shielding effects that hinder accessibility of these nucleoside triphosphates, the effective concentration is further reduced.

Preventing an Elongated Nucleic Acid from Shifting in the Polymerase Catalytic Site An additional termination effect of polymerase-nucleotide conjugates can be achieved by choosing a linker and attachment position that prevent an extended (and thus tethered) nucleic acid from shifting its tethered 3' end to the position where its 3' OH can be activated to attack an incoming nucleoside triphosphate. This effect may be achieved if the tethered nucleoside triphosphate can access the nucleoside triphosphate binding site of the polymerase but cannot reach a position where its 3' OH would correspond to the 3' OH of an incoming nucleic acid.

Application of Polymerase-Nucleotide Conjugates to De Novo Nucleic Acid Synthesis Described herein is a method for the de novo synthesis of nucleic acids using conjugates comprising a polymerase and a nucleoside triphosphate. In some embodiments of the method, conjugates comprise the polymerase Terminal deoxynucleotidyl Transferase (TdT). In other embodiments, the method may employ conjugates comprising another template-independent polymerase or a template-dependent polymerase.

Figure 1A:
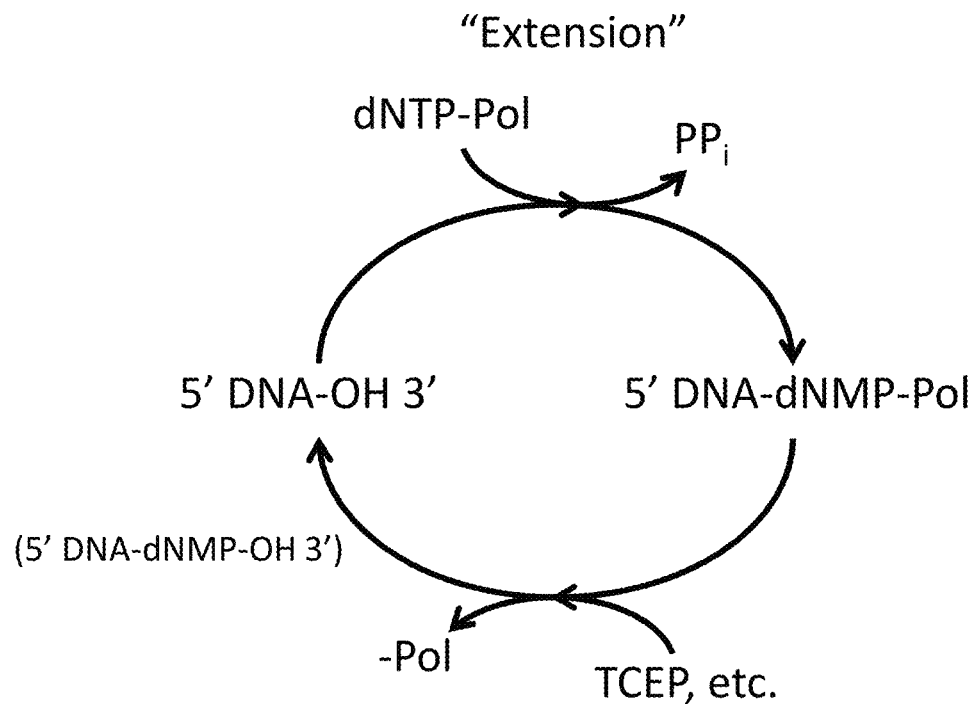
FIG. 1A. Scheme for two-step cyclic nucleic acid synthesis using polymerase-nucleotide conjugates. In the first step, a conjugate elongates a DNA molecule using its linked dNTP moiety; in the second step the linkage between the polymerase and the elongated DNA molecule is cleaved, deprotecting the DNA molecule for subsequent elongation.
Figure 1B:
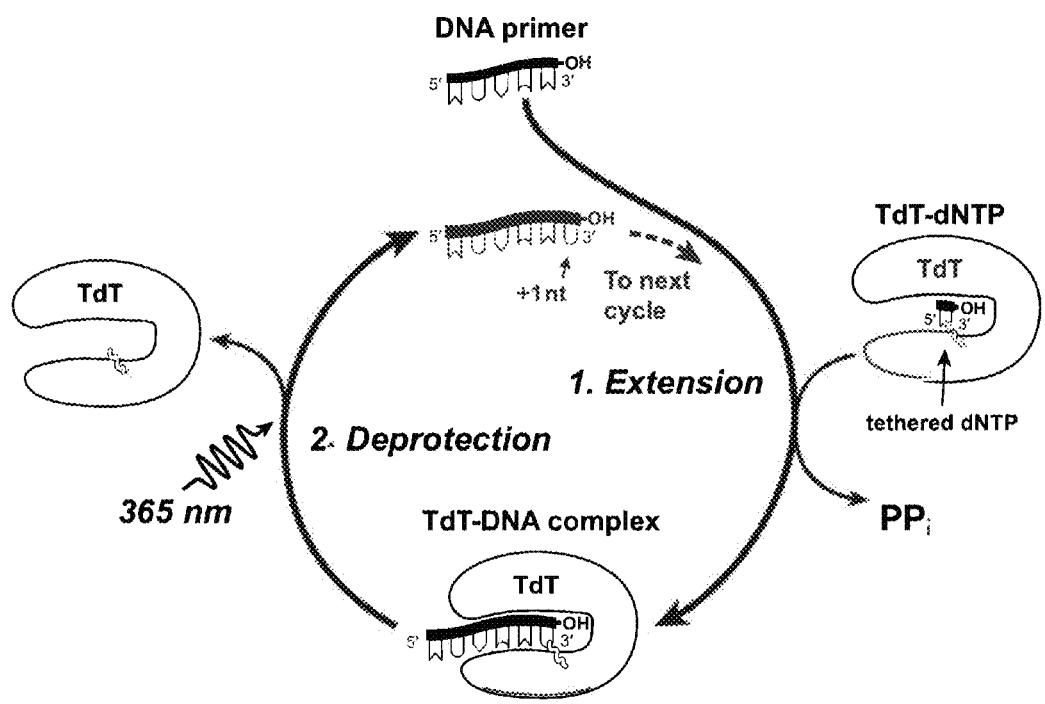
FIG. 1B. Scheme for two-step cyclic nucleic acid synthesis using TdT-dNTP conjugates comprising a TdT molecule site-specifically labeled with a dNTP via a cleavable linker.

FIG. 1A illustrates a typical process for the stepwise synthesis of a defined sequence using a template-independent polymerase. A nucleic acid that serves as an initial substrate for elongation (i.e. "starter molecule") is incubated with a first polymerase-nucleotide conjugate. Once the nucleic acid has been elongated by the tethered nucleotide of a conjugate, no further elongations occur because the conjugates implement a termination mechanism, e.g. based on the shielding effect. In the second step of the process, the linker is cleaved to release the polymerase and reverse the termination mechanism, thus enabling subsequent elongations. The elongation products are then exposed to the second conjugate, and these two steps are iterated to elongate the nucleic acid by a defined sequence. FIG. 1B illustrates a synthesis procedure using a conjugate comprising TdT and a photocleavable linker as practiced in Example 2. As described above, other strategies are available for the attachment and cleavage of the linker.

For DNA synthesis applications, in particular template-independent polymerases, i.e., a terminal deoxynucleotidyl transferase or DNA nucleotidylexotransferase, which terms are used interchangeably to refer to an enzyme having activity 2.7.7.31 may be used. Polymerases with the ability to extend single stranded nucleic acids include, but are not limited to, Polymerase Theta (Kent et al., Elife 5 (2016): e13740.), polymerase mu (Juarez et al., Nucleic acids research 34.16 (2006): 4572-4582.; or McElhinny et all., Molecular cell 19.3 (2005): 357-366.) or polymerases where template independent activity is induced, e.g. by the insertion of elements of a template independent polymerase (Juarez et al., Nucleic acids research 34.16 (2006): 4572-4582). In other DNA synthesis applications, the polymerase can be a template-dependent polymerase i.e., a DNA-directed DNA polymerase (which terms are used interchangeably to refer to an enzyme having activity 2.7.7.7 using the IUBMB nomenclature).

For RNA synthesis applications, tethered ribonucleoside triphosphates may be used. In these embodiments, a RNA specific nucleotidyl transferase, such as E. coli Poly(A) Polymerase (IUBMB EC 2.7.7.19) or Poly(U) Polymerase, among others, may be employed. The RNA nucleotidyl transferases can contain modifications, e.g. single point mutations, that influence the substrate specificity towards a specific rNTP (Lunde et al., Nucleic acids research 40.19 (2012): 9815-9824.). In some embodiments, a very short tether between an RNA nucleotidyl transferase and a ribonucleoside triphosphate may be used to induce a high effective concentration of the nucleoside triphosphate, thereby forcing incorporation of an rNTP that might not be the natural substrate of the nucleotidyl transferase.

Initial Substrates for De Novo Nucleic Acid Synthesis.

Nucleic acid synthesis schemes using polymerase tethered nucleoside triphosphates may require a nucleic acid substrate of at least 3-5 bases (or a molecule with similar properties) to initiate the synthesis. This initial substrate can then be extended nucleotide-by-nucleotide into the desired product. In some embodiments, the initial substrate may be an oligonucleotide primer synthesized using the phosphoramidite method (as demonstrated in Example 1). In some cases, the particular sequence of the initiating primer may be used in downstream applications of the synthesized nucleic acid. In some embodiments, the sequence of the initial substrate may be removed from the synthesized nucleic acid after synthesis is complete, particularly if the initial substrate comprises a cleavable linkage near it's 3' terminus. For example, if the initial substrate is a primer that has a 3' terminal deoxyuridine base, exposure of the elongated primer to USER Enzyme (i.e. a mixture of Uracil DNA glycosylase and Endonuclease VIII) will cleave the synthesized sequence from the initial substrate. However, other cleavable linkages may be used, e.g. a bridging phosphorothioate in the primer that could be cleaved with silver or mercuric ions.

In some embodiments, a double-stranded DNA molecule may be employed to initiate the synthesis, particularly if it has a 3' overhang (as demonstrated in Example 2). If the initial substrate is a linearized plasmid backbone, the DNA synthesis method could be used to elongate the DNA molecule by one or more synthetic gene sequences and the elongated DNA could then be (optionally amplified and) circularized into a plasmid. In general, the methods for nucleic acid synthesis described herein enable initiation of de novo DNA synthesis from natural nucleic acid molecules;

in contrast, it is not possible to directly extend natural nucleic acid molecules by a defined sequence using the phosphoramidite method.

Strategies for Attaching a Linker to a Nucleoside Triphosphate Useful for Nucleic Acid Synthesis.

In some embodiments, cleavage of a linker attached to a nucleotide may result in the production of a natural nucleotide upon cleavage. For example a linker comprising a nitrobenzyl moiety alkylating an amine of the nucleobase may be cleaved with light, e.g. as depicted for the exocyclic amines of cytosine and adenine below, but as is applicable to any suitable nitrogen atom on any nucleobase:

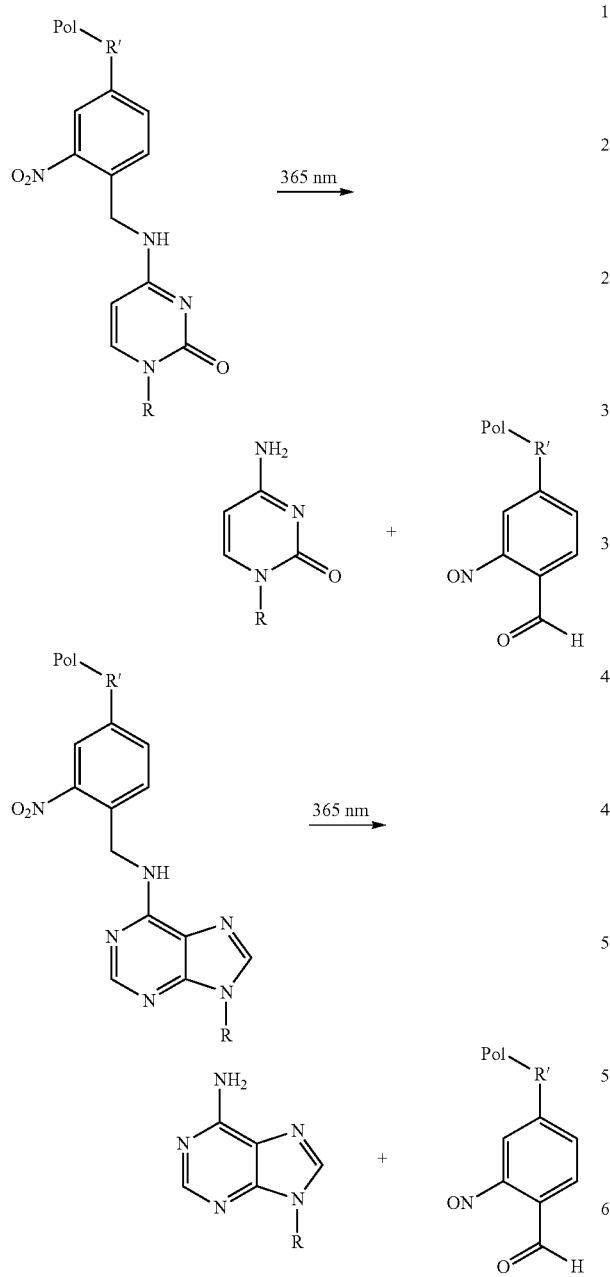

In other embodiments, a linker attached to an amine of the nucleobase via an amide linkage may be cleaved by a suitable peptidase, e.g. as depicted for the exocyclic amines of cytosine and adenine below, but is applicable to any suitable amino group on any nucleobase:

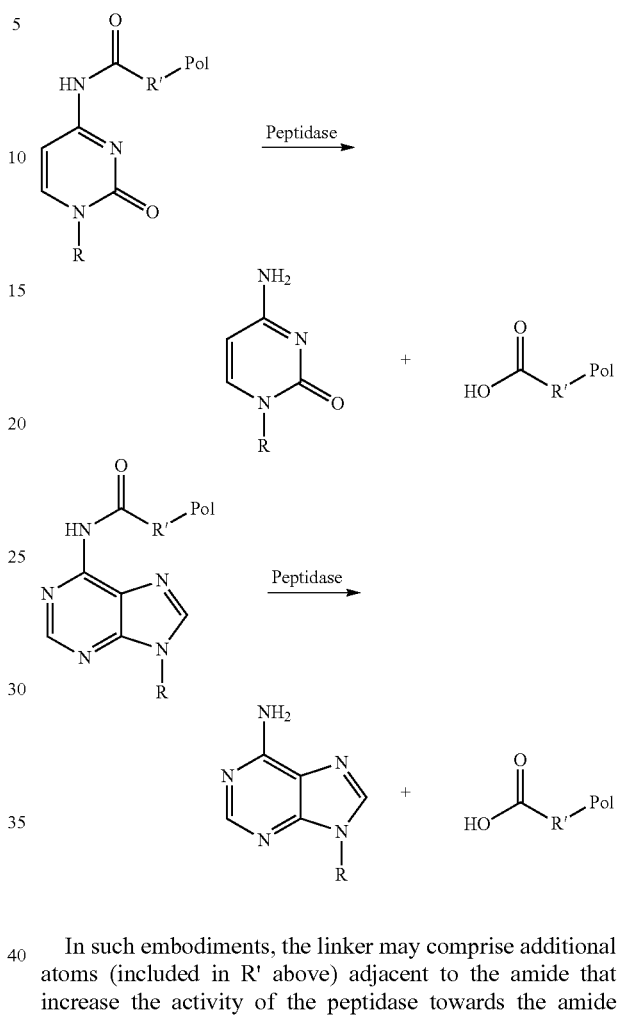

In such embodiments, the linker may comprise additional atoms (included in R' above) adjacent to the amide that increase the activity of the peptidase towards the amide bond. In some embodiments, R' is a peptide or polypeptide.

In some embodiments, cleavage of the linker in the deprotection step may leave a scar that persists throughout the stepwise synthesis but that is removed or further reduced once the stepwise synthesis is completed. This attachment strategy may enable the introduction of additional distance between the cleavable moiety of the linker and the nucleotide, which may be useful with certain (e.g. bulky) cleavable groups. Scars may be useful to prevent base pairing of incorporated nucleotides and therefore prevent the formation of secondary structures during synthesis, e.g. by preventing the exocyclic amino group from engaging in base-pairing as discussed below. Once synthesis of such a molecule is complete, a single "scar-removal" step can be used to prevent interference of the scars with downstream applications and to restore the nucleic acid's base-pairing ability.

For example, acyl scars left on the exocyclic amino group of adenine, cytosine, and guanine after cleavage may hinder the formation of some types of secondary structures during the synthesis. After the synthesis is completed, such scars may be quantitatively removed using a mild ammonia treatment (Schulhof et al., Nucleic Acids Research. 1987; 15(2):397-416.) as depicted below:

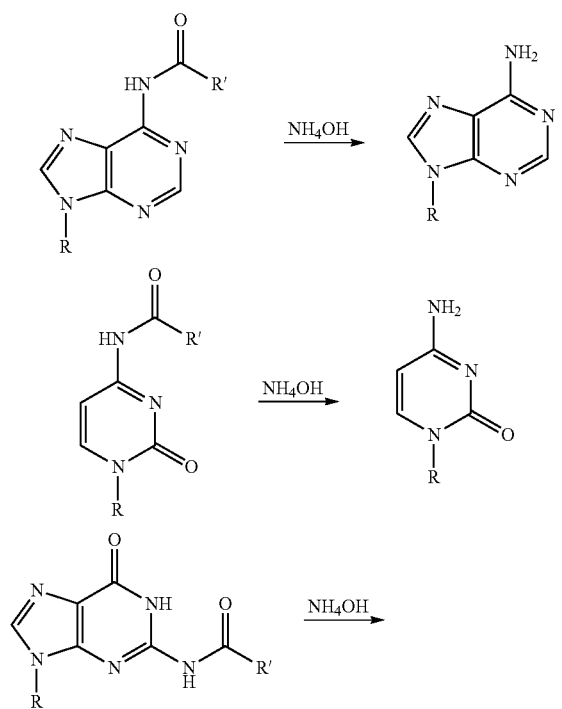

An example of a linker employing these groups would be to attach a linker comprising a 2-((4-(disulfaneyl)butanoyl)oxy)acetyl group to an exocyclic amino group of a nucleobase (forming an amide), as depicted for cytosine and adenine below:

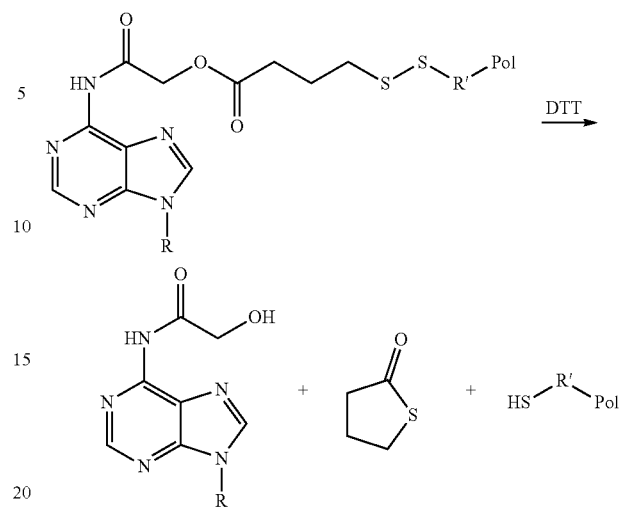

Cleavage of the disulfide (e.g. by DTT) may result in elimination of a 2-oxothiolane by intramolecular thiolactonization, leaving a glycolyl scar. Another example of this strategy would be to attach a linker comprising a photocleavable group (e.g. NPPOC) to a glycolyl of an exocyclic amino group of a nucleobase, as depicted for cytosine and adenine below:

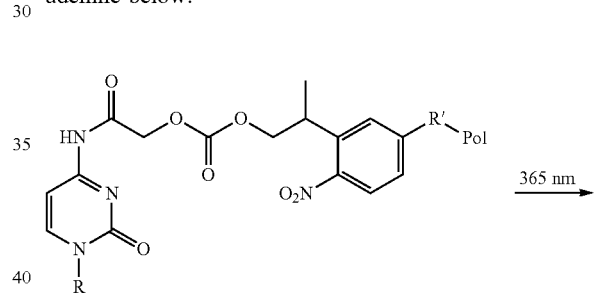

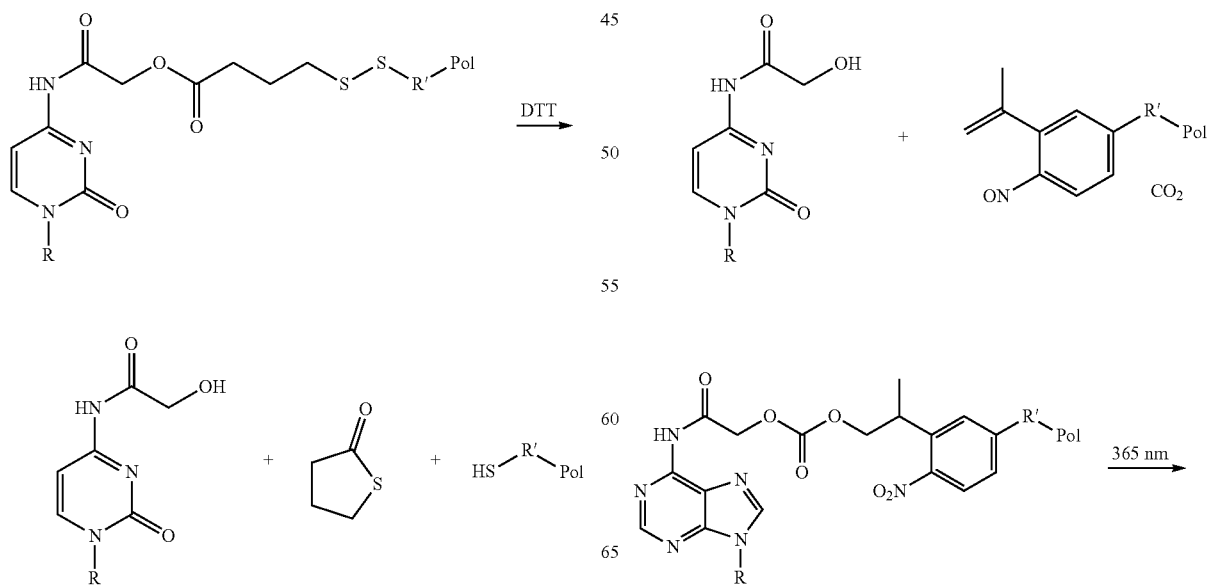

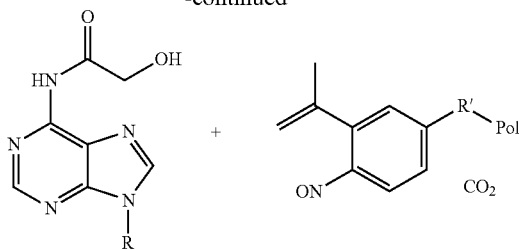

After photo-cleavage of the linker, the bases still comprise a glycolyl (acyl) scar which may not terminate further elongation by other nucleotide-polymerase conjugates, but may ultimately be removed by treatment with ammonia, as depicted below:

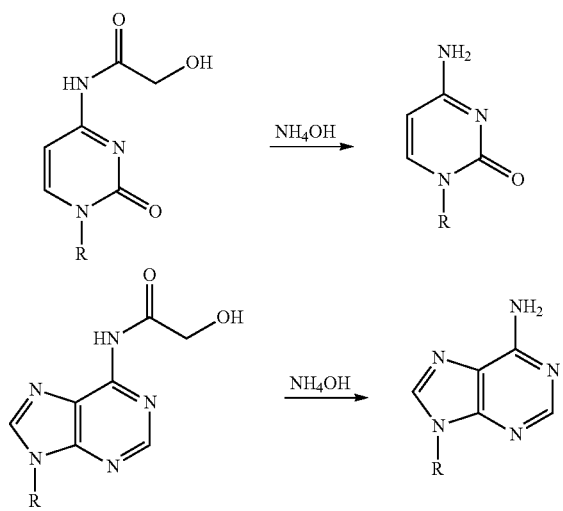

Other strategies for the attachment of the nucleoside triphosphate to the polymerase following the above described principles may be used and will be apparent to those skilled in the art.

Template independent polymerases may have a high tolerance for base modifications (e.g., for TdT see Figeys et al. (Anal Chem. 1994 Dec. 1; 66(23):4382-3.) and Li et al. (Cytometry. 1995 Jun. 1; 20(2):172-80.)) so that certain scars may be well tolerated in following nucleic acid extension steps.

In some embodiments, linkers with multiple cleavable groups inserted in tandem may be used to increase the cleavage rate compared to a linker with single cleavable group.

Mitigating the Inhibitory Effects of 3' Terminal Secondary Structure

In certain embodiments, modified nucleoside triphosphates with attached chemical moieties that prevent base pairing or the formation of undesirable secondary structure during synthesis may be used. Such modifications may include, but are not limited to, N3-methylation of cytosine, N1-methylation of adenine, O6-methylation of guanine, and acetylation of the exocyclic amine of guanine. Similar modifications were shown to significantly enhance the rate of dGTP homopolymer synthesis using TdT (Lefler and Bollum, Journal of Biological Chemistry 244.3 (1969): 594-601.). After completion of the synthesis, such base modifications may be simultaneously removed to restore base pairing for downstream applications. For example, N-acetylation of guanine may be removed by ammonia treatment as described above. N3-methylation of cytosine and N1-methylation of adenine may be removed by the enzyme AlkB, and O6-methylation of guanine may be removed by the enzyme MGMT, as depicted below:

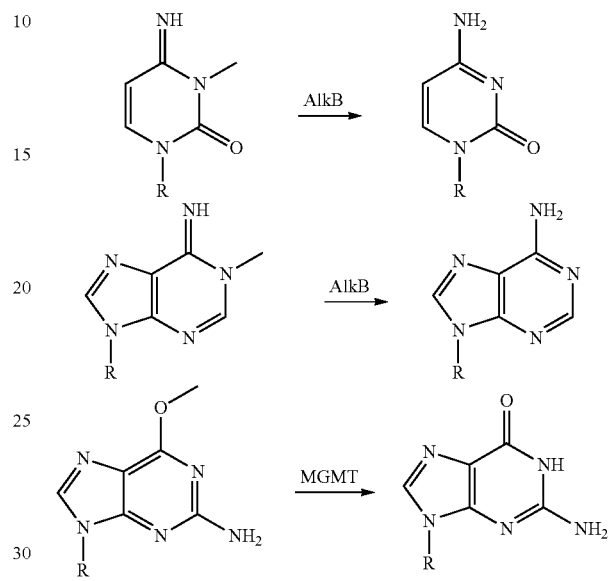

In some embodiments, the de novo nucleic acid synthesis may be paused at an intermediate step and synthesis of complementary DNA may be performed, e.g. by hybridization of a suitable primer (e.g. random hexamers) that may be extended by a template-dependent polymerase using nucleoside triphosphates. After the complementary DNA synthesis, the de novo DNA synthesis may resume, and the double stranded part of the nucleic acid may be hindered from forming secondary structures. In some cases, the complementary DNA synthesis step may comprise leaving a 3' overhang on the de novo synthesized nucleic acid to enable efficient subsequent extensions by polymerase-nucleotide conjugates.

In some embodiments, single-stranded binding proteins (e.g. *E. coli* SSB) may be included in extension reactions to hinder the formation of secondary structures in the nucleic acid being synthesized.

Incorporation of Unnatural or Modified dNTPs.

Conjugates useful for de novo nucleic acid synthesis may comprise nucleoside triphosphate analogs, including nucleotides without base-pairing ability (e.g. abasic nucleotide analogs) or nucleoside triphosphates with base-pairing ability different from the natural nucleotides, e.g. deoxyinosine or nitroindole nucleoside triphosphates.

Automation of De Novo Nucleic Acid Synthesis Using Polymerase-Nucleotide Conjugates In some embodiments, during synthesis the nucleic acid molecules are immobilized on a solid support that can be washed and exposed to the reaction cycle enzymes and buffers via automated liquid handing equipment. Examples of a solid support include, but are not limited to, a microtiter plate, into which reagents could be dispensed and removed by a liquid-handling robot, magnetic beads, which can be magnetically separated from a suspension and then resuspended in a new reagent in microtiter format, or an interior surface of a microfluidic device that can dispense the reaction cycle reagents to that location in an automated fashion.

An application of an automated system for nucleic acid synthesis employing conjugates comprising a polymerase and a nucleoside triphosphate is the synthesis of 10-100 nt oligonucleotides for molecular biology applications such as PCR. Another application is the picomole-scale or femtomole-scale synthesis of 50-500 nt or longer oligonucleotides using inkjet-based liquid handling techniques to produce DNA molecules that serve, e.g. as input to conventional DNA assembly methods (Kosuri and Church, Nature methods 11.5 (2014): 499-507.).

Figure 6:
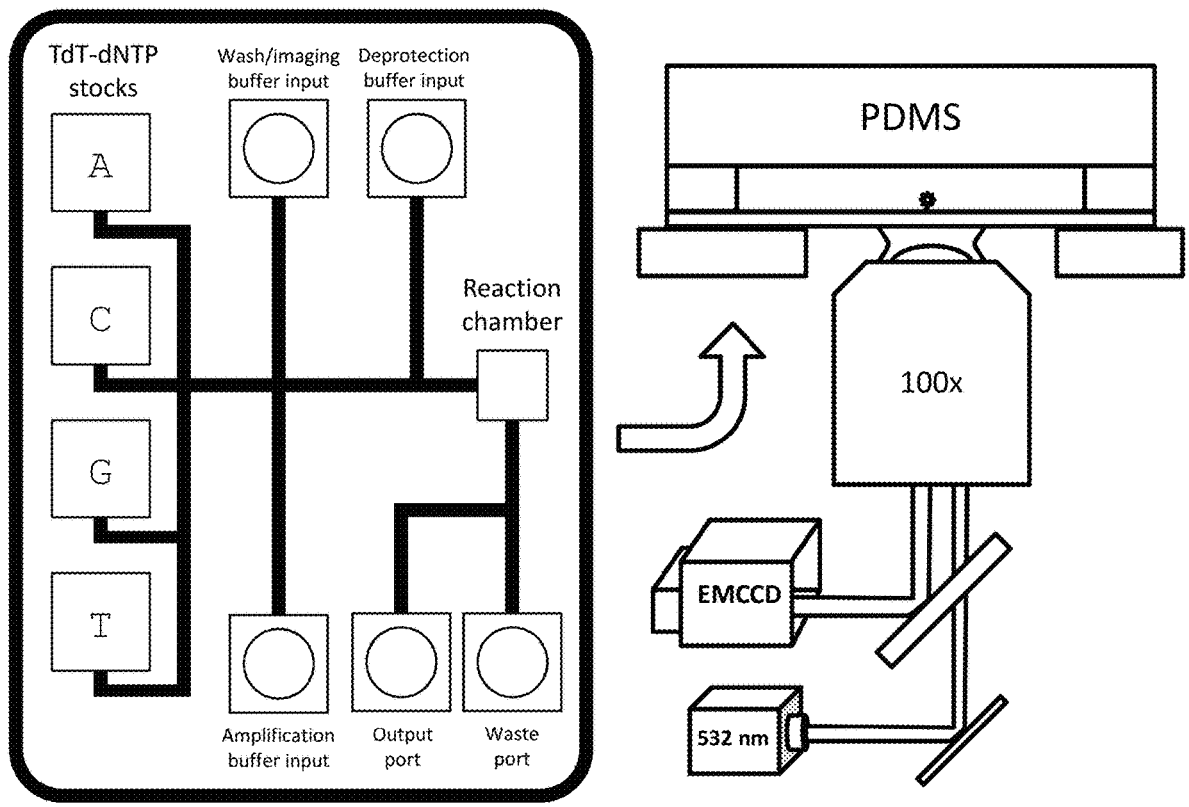
FIG. 6. Schematic drawing of an integrated microfluidic device for DNA synthesis using fluorescent polymerase-nucleotide conjugates detectible by TIRF microscopy.
Figure 7A:
FIGS. 7A-7E. Scheme for DNA sequencing using fluorescent polymerase-nucleotide conjugates.
Figure 7B:
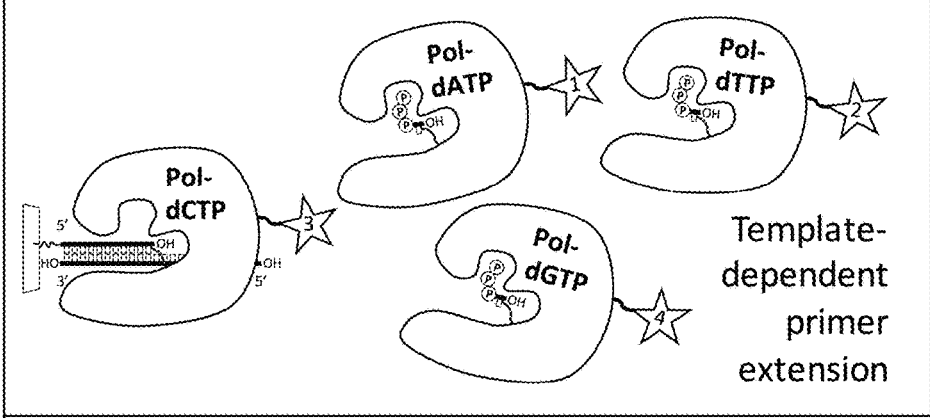
Figure 7C:
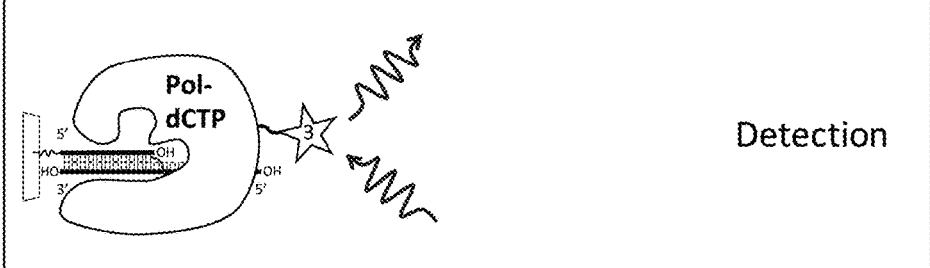
Figure 7D:
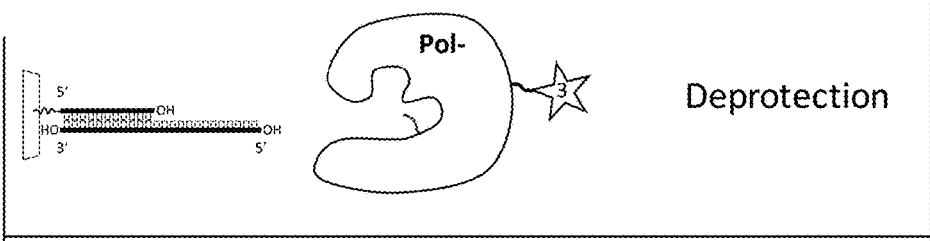
Figure 7E:
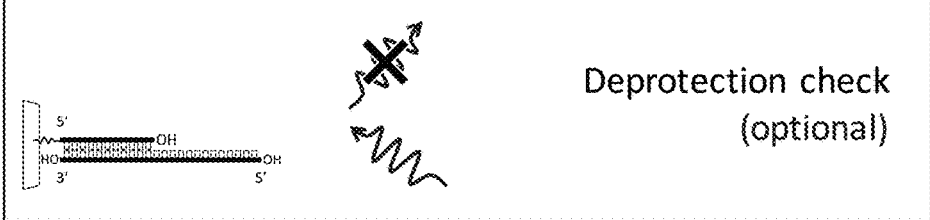

Single-Molecule Nucleic Acid Synthesis Using Fluorescent Polymerase-Nucleotide Conjugates In some embodiments, the DNA synthesis method can be implemented in single-molecule format. In this approach, the reaction chamber of an automated microfluidic device is loaded with a single primer molecule of DNA that is iteratively extended into the desired sequence using a modified version of the reaction cycle described above (FIG. 5A). In this system, the conjugates comprising a polymerase and a nucleoside triphosphate are labeled with one or more reporter molecules (e.g. fluorophores) such that once a labeled conjugate molecule has extended the primer by its tethered nucleotide and thereby becomes attached to the solid support via the primer (FIG. 5B), the growing DNA molecule becomes fluorescent. After washing away the free conjugate molecules, the polymerase attached to the primer can be detected, e.g., using a fluorescence microscopy technique such as total internal reflection fluorescence (TIRF) microscopy (FIG. 5C). After each attempted extension, the reaction chamber is washed and imaged, and if the extension is determined to have failed, it is re-attempted with the same type of conjugate. After a successful extension is confirmed, the deprotection reagent is introduced to the reaction chamber, cleaving the tethered labeled polymerase and thereby both deprotecting the 3' end of the growing DNA molecule for subsequent extension and simultaneously rendering it non-fluorescent (FIG. 5D). If the deprotection fails, the fluorescence signal will remain, and the deprotection step is reattempted (FIG. 5E). These extension and deprotection checks prevent the introduction of deletion errors that inevitably accumulate during bulk reactions that fail to go to 100% completion. An automated synthesizer executing this scheme will eventually synthesize one DNA molecule with the desired sequence that can subsequently be amplified. An example of such a synthesizer is depicted in FIG. 6. The synthesizer comprises a PDMS device with input ports for reagents, including a port for each polymerase-nucleotide conjugate, a port for the wash buffer, a port for the deprotection buffer, and a port for the in situ amplification buffer. The input ports are connected via microchannels (and, optionally, computer-actuated microvalves) to a reaction chamber where the synthesis takes place. The device also comprises a waste port and an output port (for collecting the synthesized products) connected to the reaction chamber my microchannels. The device may be mounted on a microscope suitable for single-molecule imaging, e.g. the objective-style TIRF microscope indicated in FIG. 6. The fluorophores attached to the conjugates may be excited by a laser of a suitable wavelength, e.g. 532 nm; emitted light may be collected by an objective and imaged on a suitable detector, e.g. an electron-multiplying charge coupled-device (EMCCD) camera connected to a computer. The computer may execute the synthesis scheme described above by (a) interpreting the signals from the detector using an algorithm and (b) dispensing the appropriate reagent to the reaction chamber by actuating microvalves or pumps within or outside of the microfluidic device.

Methods for DNA Sequencing Using Polymerase-Nucleotide Conjugates.

Provided herein is a method for nucleic acid sequencing using conjugates of a template-dependent polymerase and a nucleoside triphosphate. The method is analogous to Sequencing By Synthesis (SBS).

In some embodiments, the method employs an "ACGT extension reagent" comprising four conjugates with base-pairing ability equivalent to A, C, G, and T, wherein the conjugates are labeled with distinguishable labels, e.g. distinct fluorophores. In other embodiments, the method employs "four distinct extension reagents" in separate containers, each comprising a conjugate with base-pairing ability equivalent to A, C, G, and T respectively. In some embodiments, these four extension reagents may be labeled for detection, e.g. with fluorophores.

In some embodiments, the method comprises: (a) immobilizing a duplex comprising a primer and template nucleic acid on a support (b) exposing the duplex to the "ACGT extension reagent" to extend the primer by a nucleotide complementary to the template; (c) detecting the label of the attached conjugate to infer the complementary base of the template; (d) exposing the duplex to the deprotection reagent, which cleaves the linkage between the polymerase and the added nucleotide, rendering the duplex unlabeled; and (e) repeating steps (b-d) 10 or more times to determine the sequence of at least part of the template molecule. An example of this method employing polymerase-conjugates with four distinguishable fluorophores is depicted in FIGS. 7A-7E.

In other embodiments, the method comprises: (a) immobilizing a duplex comprising a primer and template nucleic acid on a support (b) exposing the duplex to the first extension reagent to extend the primer by a nucleotide complementary to the template if the nucleotide of the conjugate is complementary; (c) detecting the label of the attached conjugate to infer if an extension has occurred; (d) exposing the nucleic acid to the deprotection reagent, which cleaves the linkage between the polymerase and the added nucleotide, rendering the duplex unlabeled; (e) repeating steps (b-d) three more times with the remaining three extension reagents, and (f) repeating steps (b-e) 10 or more times to determine the sequence of at least part of the template molecule.

In some embodiments, the detectible label may be a fluorescent protein fused to the polymerase. In other embodiments, the detectible label may be a quantum dot that is specifically attached to the polymerase.

Particularly in embodiments that employ four distinct extension reagents, the conjugates may be non-fluorescent or without a detectible label. In such embodiments, extension may be detected by other signals of the extension reaction such as release of $H^+$ or pyrophosphate. In other embodiments, the polymerase may be fused to a reporter enzyme such as luciferase or peroxidase that may be detected when they produce light by catalyzing a reaction. In other embodiments, the polymerase may be fused to a nanoparticle detectible by scatting light. In other embodiments, an otherwise unlabeled polymerase of a conjugate that has extended a nucleic acid may be detected by a change in surface plasmon resonance.

Particularly in embodiments that employ conjugates with detectible labels, the method may be useful for determining the sequence of individual molecules, i.e. "single-molecule sequencing".

In some embodiments, the method may additionally comprise an initial step of making 10, 100, 1000, or more copies of the template molecule and then applying a method described above to all copies simultaneously.

In any embodiment of the nucleic acid sequencing method, the length of the linker between the nucleoside triphosphate and the polymerase of the conjugates may be selected to maximize the fidelity of nucleotide incorporation by the conjugates, i.e. to minimize incorporation of mismatched bases with the template. Likewise, in any embodiment, the concentration of divalent cation(s) in the extension reaction (e.g. $Mg^{2+}$) may be adjusted to maximize the fidelity of nucleotide incorporation by the conjugates.

In some embodiments, the polymerase of the conjugates may be a polymerase with "random binding order", i.e. the primer-template duplex can bind to the catalytic site before or after nucleoside triphosphate.

In other embodiments, the polymerase of the conjugates may be a polymerase with defined binding order, i.e. the primer-template duplex must bind to the catalytic site before the nucleoside triphosphate. In such embodiments, the length of the linker between the nucleoside triphosphate and the polymerase of the conjugates may be selected to minimize inhibition of primer-template duplex binding to the conjugate, i.e. by using a linker longer than 10 Å, or 100 Å, or 200 Å.

In any embodiment, the conjugate may comprise a reversible terminator nucleoside triphosphate.

EMBODIMENTS

Embodiment 1. A conjugate comprising a polymerase and a nucleoside triphosphate, wherein the polymerase and the nucleoside triphosphate are covalently linked via a linker that comprises a cleavable linkage.

Embodiment 2. The conjugate of embodiment 1, wherein the polymerase is capable of catalyzing the addition of the nucleotide that is linked to the polymerase to the 3' end of a nucleic acid.

Embodiment 3. The conjugate of any prior embodiment, wherein the polymerase is linked to the nucleoside triphosphate via a linker that has a length in the range of 4-100 Å, and wherein the length of the linker is sufficient for the nucleoside triphosphate to access the active site of the polymerase.

Embodiment 4. The conjugate of any prior embodiment, wherein the nucleoside triphosphate is linked to a cysteine residue in the polymerase.

Embodiment 5. The conjugate of any prior embodiment, wherein the cleavable linkage is a light or enzyme-cleavable linkage.

Embodiment 6. The conjugate of any prior embodiment, wherein the polymerase is a DNA polymerase.

Embodiment 7. The conjugate of any of embodiments 1-5, wherein the polymerase is an RNA polymerase.

Embodiment 8. The conjugate of any prior embodiment, wherein the polymerase is a template-independent polymerase.

Embodiment 9. The conjugate of any of embodiments 1-7, wherein the polymerase is a template-dependent polymerase.

Embodiment 10. The conjugate of any prior embodiment, wherein the nucleoside triphosphate or the polymerase comprises a fluorescent label.

Embodiment 11. The conjugate of any prior embodiment, wherein the nucleoside triphosphate is a deoxyribonucleoside triphosphate.

Embodiment 12. The conjugate of any prior embodiment, wherein the nucleoside triphosphate is a ribonucleoside triphosphate.

Embodiment 13. A set of conjugates of any prior embodiment, wherein the conjugates correspond to G, A, T and C and are in separate containers.

Embodiment 14. A method of nucleic acid synthesis, comprising:

incubating a nucleic acid with a first conjugate, wherein the first conjugate is a conjugate of any prior embodiment and the incubating is done under conditions in which the polymerase catalyzes the covalent addition of the nucleotide of the first conjugate onto the 3' hydroxyl of the nucleic acid, to make an extension product.

Embodiment 15. The method of embodiment 14, wherein nucleic acid is tethered to a support.

Embodiment 16. The method of embodiment 14 or 15, wherein the method comprises, after addition of the nucleotide onto the nucleic acid, cleaving the cleavable linkage of the linker, thereby releasing the polymerase from the extension product.

Embodiment 17. The method of embodiment 16, wherein the cleavable linkage is an enzyme- or light-cleavable linkage and the cleaving comprises exposing the extension product to an enzyme or to light.

Embodiment 18. The method of embodiments 16 or 17, wherein the cleavage of the cleavable linkage deprotects the added nucleotide to produce a deprotected extension product.

Embodiment 19. The method of embodiment 18, further comprising, after deprotection of the added nucleotide:

incubating the deprotected extension product with a second conjugate, wherein the second conjugate is a conjugate of any of embodiments 1-12 and the incubating is done under conditions in which the polymerase catalyzes the covalent addition of the nucleotide of the second conjugate onto the 3' end of the deprotected extension product.

Embodiment 20. The method of any of embodiments 14-19, wherein the method comprises:

(a) incubating a nucleic acid with a first conjugate of any of embodiments 1-12 under conditions in which the polymerase catalyzes the covalent addition of the nucleotide of the first conjugate onto the 3' hydroxyl of the nucleic acid, to make an extension product;

(b) cleaving the cleavable linkage of the linker, thereby releasing the polymerase from the extension product and deprotecting the extension product;

(c) incubating the deprotected extension product with a second conjugate of any of embodiments 1-12 under conditions in which the polymerase catalyzes the covalent addition of the nucleotide of the second conjugate onto the 3' end of the extension product, to make a second extension product;

(d) repeating steps (b)-(c) on the second extension product multiple times to produce an extended nucleic acid of a defined sequence.

Embodiment 21. The method of embodiment 20, wherein the nucleotide is a reversible terminator, and wherein deprotection of the extension product comprises removal of the blocking group of the reversible terminator.

Embodiment 22. The method of any of embodiments 14-21, wherein the nucleic acid is an oligonucleotide.

Embodiment 23. A method of sequencing, comprising:

incubating a duplex comprising a primer and a template with a composition comprising a set of conjugates of embodiment 13, wherein the conjugates correspond to G, A, T (or U) and C and are distinguishably labeled;

detecting which nucleotide has been added to the primer by detecting a label that is tethered to the polymerase that has added the nucleotide to the primer;

deprotecting the extension product by cleaving the linker; and repeating the incubation, detection and deprotection steps to obtain the sequence of at least part of the template.

Embodiment 24. The method of embodiment 23, wherein the method of sequencing is a method of DNA sequencing.

Embodiment 25. The method of embodiment 23, wherein the method of sequencing is a method of RNA sequencing.

Embodiment 26. The method of any of embodiments 23-25, wherein the nucleotide is a reversible terminator, and wherein deprotection of the extension product comprises removal of the blocking group.

Embodiment 27. A reagent set, comprising:

a polymerase that has been modified to contain a single cysteine on its surface; and a set of nucleoside triphosphates, wherein each of the nucleoside triphosphates is linked to a sulfhydryl-reactive group.

Embodiment 28. The reagent set of embodiment 27, wherein the nucleoside triphosphates correspond to G, A, T (or U) and C.

Embodiment 29. The reagent set of any of embodiments 27-28, wherein the nucleoside triphosphates are reversible terminators.

Embodiment 30. The reagent set of any of embodiments 27-29, wherein the nucleoside triphosphates comprise a linker that has a length in the range of 4-100 Å.

EXAMPLES

Aspects of the present teachings can be further understood in light of the following examples, which should not be construed as limiting the scope of the present teachings in any way.

Example 1

Tethered Nucleotide Incorporation by Polymerase-Nucleotide Conjugates Employing a Linker Cleavable by Reducing Agents 1. Generation of Polymerase (TdT) Mutants with Various Attachment Positions for the Linker.

A gBlock coding for the *Mus musculus* TdT amino acid sequence used by Boulé et al. (Molecular biotechnology 10.3 (1998): 199-208.) was ordered from IDT (Coralville, Iowa). The sequence was cloned into a pET19b vector, fusing the N-terminal his-tag of the vector to the protein using isothermal assembly. QuickChange PCR was used to generate a TdT mutant lacking all surface cysteines that might allow incorporation of tethered dNTPs (TdT5cysX). The cysteines in positions 188, 302, and 378 were mutated into alanine, the cysteines in positions 216 and 438 were mutated into serine (positions refer to the numbering in PDB structure 4I27). TdT mutants containing one surface cysteine close to the catalytic site were generated by QuickChange PCR on TdT5cysX. Cysteines were inserted in positions 188, 302, 180 or 253, respectively.

Listed below is the amino acid sequence of the "wildtype" TdT protein used in this example prior to the mutation of cysteine residues (TdTwt):

(SEQ ID NO: 1)
MGHHHHHHHHHHSSGHIDDDDKHMSQYACQRRTTLNNHNQIFTDAFDIL

AENDEFRENEGPSLTFMRAASVLKSLPFTIISMKDIEGIPNLGDRVKSI

IEEIIEDGESSAVKAVLNDERYKSFKLFTSVFGVGLKTSEKWFRMGFRT

LSNIRSDKSLTFTRMQRAGFLYYEDLVSRVTRAEAEAVGVLVKEAVWAS

LPDAFVTMTGGFRRGKKTGHDVDFLITSPGATEEEEQQLLHKVISLWEH

KGLLLYYDLVESTFEKLKLPSRKVDALDHFQKCFLILKLHHQRVDSDQS

SWQEGKTWKAIRVDLVVCPYERRAFALLGWTGSRQFERDLRRYATHERK

MIIDNHALYDKTKRIFLEAESEEEIFAHLGLDYIEPWERNA.

As described above, plasmids coding for 6 TdT mutants with varying cysteine residues (therefore with different attachment positions for a linker) were generated:
(a) A plasmid coding for "wildtype" TdT with 7 cysteines (TdTwt)
(b) A plasmid coding for a TdT mutant with no surface cysteines and only 2 cysteines that are both buried (TdT5cysX)
(c) Four plasmids coding for TdT mutants with 2 buried cysteines plus one exposed surface cysteine in different positions (188, 180, 253, and 302) referred to herein as TdTcys188, TdTcys 180, TdTcys253, and TdTcys302

2. Protein Expression and Purification of the Mutants.

TdT expression was performed using Rosetta-gami B(DE3)pLysS cells (Novagen) in LB media containing antibiotics for all four resistance markers of the cells (Kan, Cmp, Tet, and Carb, which is introduced by the pET19 vector). An overnight culture of 50 mL was used to inoculate a 400 mL expression culture with ½₀ vol. Cells were grown at 37° C. and 200 rpm shaking until they reached OD 0.6. IPTG was added to a final concentration of 0.5 mM and the expression was performed for 12 h at 30° C. Cells were harvested by centrifugation at 8000 G for 10 min and resuspended in 20 mL buffer A (20 mM Tris-HCl, 0.5 M NaCl, pH 8.3)+5 mM imidazole. Cell lysis was performed using sonication followed by centrifugation at 15000 G for 20 min. The supernatant was applied to a gravity column containing 1 mL of Ni-NTA agarose (Qiagen). The column was washed with 20 volumes of buffer A+40 mM imidazole, and bound protein was eluted using 4 mL buffer A+500 mM imidazole. The protein was concentrated to ~0.15 mL with Vivaspin 20 columns (MWCO 10 kDa, Sartorius) and then dialyzed against 200 mL TdT storage buffer (100 mM NaCl, 200 mM K2HPO4, pH 7.5) over night using Pur-A-Lyzer™ Dialysis Kit Mini 12000 tubes (Sigma).

All 6 TdT mutants with varying cysteine residues were expressed and purified.

3. Attachment of Tethered Nucleoside Triphosphates to the Polymerase.

To prepare TdT-dUTP conjugates, the linker-nucleotide OPSS-PEG4-aa-dUTP was first synthesized and then reacted with TdT. OPSS-PEG4-aa-dUTP was synthesized by reacting amino-allyl dUTP (aa-dUTP) with the heterobifunctional crosslinker PEG4-SPDP (FIG. 3A). The reaction contained 12.5 mM aa-dUTP, 3 mM PEG4-SPDP crosslinker and 125 mM sodium bicarbonate (ph 8.3) in a volume of 8 μL and was performed at RT for 1 h. The reaction was quenched by the addition of 1 μL of 100 mM glycine in PBS for 10 min. The buffer was adjusted to the OPSS-labeling conditions by the addition of 1 μL 10×TdT storage buffer and then 70-100 μg purified protein in 40 μL 1×TdT storage buffer were added. The reaction to attach the linker-nucleotide to TdT was performed at RT for 13 h. Removal of free (i.e. unattached) linker-nucleotides was conducted using the Capturem His-Tagged Purification Miniprep Kit (Clonetech). Purification resulted in protein concentrations between 0.2 and 0.4 μg/μL. Dialysis against 100 mL 1×TdT reaction buffer (NEB) was performed in Pur-A-Lyzer™ Dialysis Kit Mini 12000 tubes for 4 h.

The scheme for the preparation of the polymerase-nucleotide conjugates is shown in FIG. 3. First, the aminoallyl dUTP (aa-dUTP) is reacted with the heterobifunctional amine-to-thiol crosslinker PEG4-SPDP (panel A) to form the thiol-reactive linker-nucleotide OPSS-PEG4-aa-dUTP (panel B). OPSS-PEG4-aa-dUTP can then be used to site-specifically label TdT at surface cysteine residues (panel C) via disulfide bond formation.

All 6 TdT mutants with varying cysteine residues were separately exposed to OPSS-PEG4-aa-dUTP tethering reactions.
(a) TdTwt contains five surface cysteine residues that result in labeling with up to five OPSS-PEG4-aa-dUTP moieties.
(b) TdT5cysX only contains two buried but no surface cysteine residues, presumably not resulting in substantial labeling by OPSS-PEG4-aa-dUTP.
(c) TdTcys188, TdTcys180, TdTcys253, and TdTcys302 have a single surface cysteine that can be labeled with a single OPSS-PEG4-aa-dUTP moiety (at residue position 188, 180, 253, and 302, respectively). These TdT mutants also contain the two buried cysteines present in TdT5cysX that presumably are not labeled.

4. Generation of the Ladder of Elongation Product Standards.

The ladder of linked incorporation product standards was generated by incorporating free OPSS-PEG4-aa-dUTP using TdT. The reaction to synthesize OPSS-PEG4-aa-dUTP was performed by mixing 6 μL 50 mM aa-dUTP, 5 μL 180 mM PEG4-SPDP, 5 μL 1M NaHCO$_3$ and 4 μL ddH$_2$O. The reaction was incubated at RT for 1 h and another 5 μL of 180 mM PEG4-SPDP was added. After 1 h, the reaction was quenched using 5 μL of 100 mM glycine in PBS. To achieve varying numbers of incorporations, 6 TdT incorporation reactions using free OPSS-PEG4-aa-dUTP as substrate were performed. The reactions contained 1.5 μL 10×NEB TdT reaction buffer, 1.5 μL NEB TdT CoCl$_2$, 1.5 μL 10 μM 5'-FAM labeled 35-mer dT-oligonucleotide (5'-FAM-dT (35)), 1 μL 10 mM OPSS-PEG4-aa-dUTP, 4.5 μL ddH$_2$O and varied in their TdT concentration (100, 50, 25, 12.5, 6.3, 3.13 units of NEB TdT in 5 μL 1×NEB reaction buffer). Reactions were performed for 5 min at 37° C. and stopped by the addition of 0.3 mM EDTA. Before running the ladder on the polyacrylamide gel, reaction products were mixed with an equal volume of 2×Novex Tris-Glycine buffer+1% v/v β-mercaptoethanol and heated to 95° C. for 5 min.

Figure 8A:
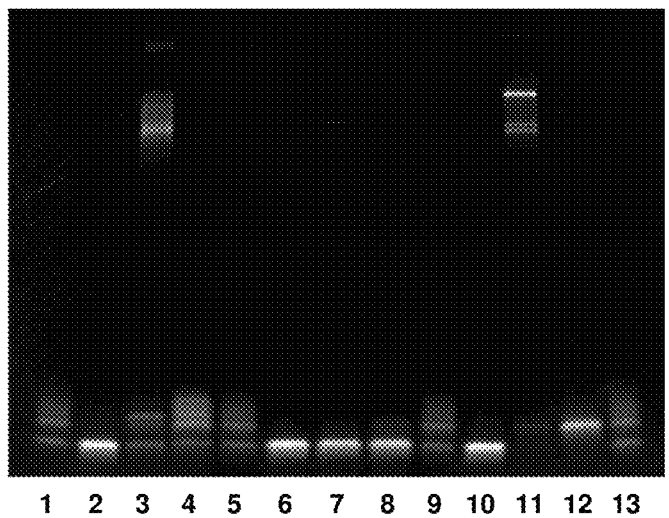
FIGS. 8A-8B Demonstration of elongation of a primer by polymerase-nucleotide conjugates with varying numbers of tethered nucleotides on SDS-PAGE.

The 5'-FAM-dT$_{(60)}$ oligo was extended by 0 to 5 or more OPSS-PEG4-aa-dUMP nucleotides. After reduction of the ladder in the loading dye, the HS-PEG4-aa-dUTP elongation product standards (structure of one HS-PEG4-aa-dUTP elongation product is depicted in FIG. 3E) were resolved on a polyacrylamide gel (FIGS. 8A and B, lanes labeled "L"). The ladder was used to identify the cleaved products of primer elongation reactions with polymerase-nucleotide conjugates by comparison of the migration of the elongation product bands to the ladder bands.

5. Incorporation of Tethered Nucleoside Triphosphates into a Nucleic Acid.

Figure 8B:
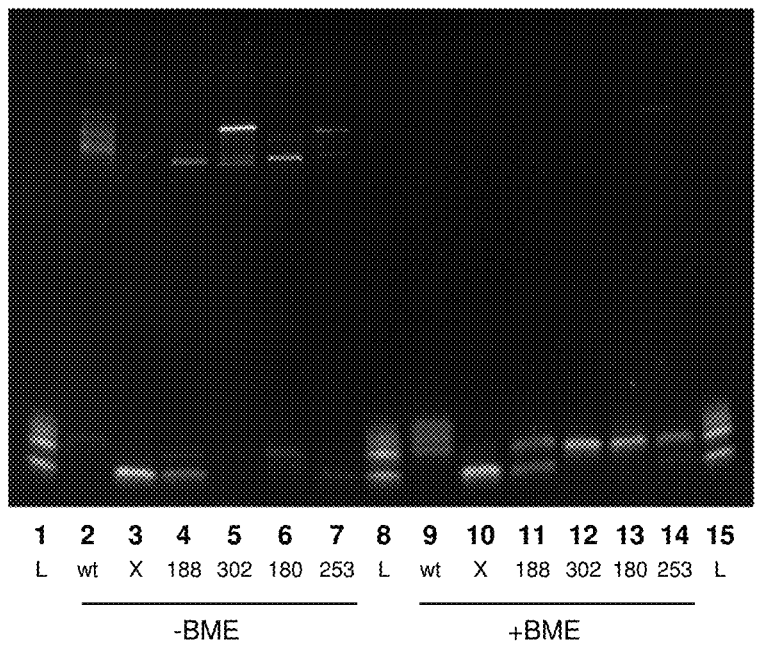

The OPSS-PEG4-aa-dUTP conjugates of TdTwt, TdT5cysX, TdTcys188, TdTcys180, TdTcys253, and TdTcys302 were reacted with 5'-FAM-dT(35). Reactions that are shown in FIG. 8A contained 1 μL of 5 μM 5'-FAM-dT(35), 17 μL of the purified, conjugated TdT variants in 1×TdT reaction buffer (NEB) and 2 μL of 2.5 mM CoCl$_2$. The reactions were performed for 20 sec at 37° C. and then quenched by the addition of 33 mM EDTA. Reactions shown in FIG. 8B contained 1.5 μL of 5 μM 5'-FAM-dT(35), 1 μL 10×NEB reaction buffer, 1.5 μL of 2.5 mM CoCl$_2$, 5 μL of the respective TdT conjugate in 1×TdT buffer and 6 μL ddH$_2$O. Reactions were performed at 37° C. for 40 sec, quenching was performed by the addition of 33 mM EDTA. To prepare the reactions for the gel, samples were mixed with the equivalent volume of 2×Novex Tris-Glycine SDS Sample Buffer (Thermo Scientific), or with 2×Novex Tris-Glycine buffer+1% v/v 2-mercaptoethanol (BME), respectively. All samples were heated to 95° C. for 5 min and run on SDS.

As shown in chemical detail in FIG. 3, TdT conjugates of OPSS-PEG4-aa-dUTP (panel C) can incorporate a tethered nucleotide into a primer, which results in covalent attachment of the TdT moiety to the elongated primer (panel D). For detection purposes the primer can be labeled at its 5' end with a fluorescent dye such as 6-carboxyfluorescein (FAM). The primer-polymerase complexes can be dissociated by exposure to βME, which cleaves the disulfide bond between the incorporated nucleotide and TdT, releasing free TdT and a primer that is elongated by a dUMP harboring a HS-PEG4-aa scar (panel E).

To demonstrate that polymerase-nucleotide conjugates add their tethered nucleotides to an oligonucleotide, TdT conjugates of OPSS-PEG4-aa-dUTP were incubated with a 5' FAM-labeled dT(35) primer. The reaction was performed with conjugates of TdTwt, which have multiple tethered nucleotides, conjugates of TdT5cysX, which do not have tethered nucleotides, and conjugates of TdTcys302 which has a single nucleotide tethered to the cysteine at position 302. As described above, the reactions were stopped and the products were resolved by SDS-PAGE (FIG. 8A). TdTwt and TdTcys302 conjugates added their tethered nucleotide(s) to the 3' end of the primer and became covalently linked forming a polymerase-primer complex, as indicated by much slower migration of the bands on SDS-PAGE (lanes 3 and 11, respectively) compared to the primer (lanes labeled "P": 2, 6, and 10). In contrast, no shift in migration was seen with TdT5cysX (lane 7) that does not comprise tethered nucleotides. Upon addition of the disulfide-cleaving reagent 2-mercaptoethanol, the primer-TdT complexes dissociated, as indicated by restored migration of the bands (lanes labeled "B": 4, 8, and 12 for TdTwt, TdT5cysX, and TdTcys302 respectively). The extension of the primer can be referenced to the ladder of product standards (lanes labeled "L": 1, 5, 9, and 13). Conjugates of TdTwt incorporated multiple tethered nucleotides, yielding a primer that was extended by up to 5 scarred dUMP nucleotides (lane 4). Conjugates of TdTcys302 predominantly extended the primer by a single scarred dUMP nucleotide (lane 12), and conjugates of TdT5cysX did not extend the primer (lane 8).

These data show that the polymerase moiety of polymerase-nucleotide conjugates can incorporate one or more tethered nucleoside triphosphates into a primer. They also show that conjugates labeled with a single nucleotide triphosphate can perform a single elongation of a primer and that further elongations of the primer by other polymerase-nucleotide conjugates can be hindered, enabling elongation of a nucleic acid by a single nucleotide.

To demonstrate that functional polymerase-nucleotide conjugates can be generated using a variety of attachment positions on the polymerase, OPSS-PEG4-aa-dUTP conjugates of TdT mutants with a single surface cysteine at positions 188, 302, 180, and 253 (TdTcys188, TdTcys302, TdTcys180, and TdTcys253, respectively) were used to extend a primer by a single nucleotide. The conjugates were separately exposed to a 5' fluorescently-labeled poly-dT primer. Separation of the products on SDS-PAGE (FIG. 8B) revealed that all four conjugates were able to incorporate a tethered nucleotide to the 3' end of the primer, as indicated by the formation of a much slower migrating band corresponding to the polymerase-primer complex (lanes 4-7, respectively) compared to primer band (fastest migrating band of lanes labeled "L": 1, 8, and 15). Upon cleavage of the linker by 2-mercaptoethanol (BME), the polymerase-primer complex dissociated, leaving a primer that had been predominantly extended by 1 scarred dUMP nucleotide (lanes 11-14, respectively) as identified by comparison with the ladder of product standards (lanes labeled "L").

These data show that the principle of tethering a single nucleotide to a polymerase for achieving single nucleotide elongation of a nucleic acid is generalizable across attachment points on the polymerase.

Example 2

Synthesis of a Defined DNA Sequence Using Polymerase-Nucleotide Conjugates Employing a Light-Cleavable Linker 1. Generation of an MBP-TdT Fusion Protein with Only One Surface Exposed Cysteine (TdTcys).

The sequence encoding Maltose Binding Protein (MBP) was amplified from pMAL-c5X (NEB) and N-terminally fused to the TdTcys302 construct used in Example 1 using isothermal assembly. The resulting MBP-TdT fusion protein (herein referred to as TdTcys) was used throughout Example 2.

Protein sequence of TdTcys:

```
                                           (SEQ ID NO: 2)
MGHHHHHHHHHSSGHIDDDDKHMMKIEEGKLVIWINGDKGYNGLAEVG

KKFEKDTGIKVTVEHPDKLEEKFPQVAATGDGPDIIFWAHDRFGGYAQS

GLLAEITPDKAFQDKLYPFTWDAVRYNGKLIAYPIAVEALSLIYNKDLL

PNPPKTWEEIPALDKELKAKGKSALMFNLQEPYFTWPLIAADGGYAFKY

ENGKYDIKDVGVDNAGAKAGLTFLVDLIKNKHMNADTDYSIAEAAFNKG

ETAMTINGPWAWSNIDTSKVNYGVTVLPTFKGQPSKPFVGVLSAGINAA

SPNKELAKEFLENYLLTDEGLEAVNKDKPLGAVALKSYEEELVKDPRIA

ATMENAQKGEIMPNIPQMSAFWYAVRTAVINAASGRQVDEALKDAQTNS

SSNNNNNNNNNNLGIEGRISHMSMGGRDIVDGSEFSPSPVPGSQNVPAP

AVKKISQYACQRRTTLNNYNQLFTDALDILAENDELRENEGSALAFMRA

SSVLKSLPFPITSMKDTEGIPSLGDKVKSIIEGIIEDGESSEAKAVLND
```

```
                                           -continued
ERYKSFKLFTSVFGVGLKTAEKWFRMGFRTLSKIQSDKSLRFTQMQKAG

FLYYEDLVSCVNRPEAEAVSMLVKEAVVTFLPDALVTMTGGFRRGKMTG

HDVDFLITSPEATEDEEQQLHKVTDFWKQQGLLLYADILESTFEKFKQP

SRKVDALDHFQKCFLILKLDHGRVHSEKSGQQEGKGWKAIRVDLVMSPY

DRRAFALLGWTGSRQFERDLRRYATHERKMMLDNHALYDRTKRVFLEAE

SEEEIFAHLGLDYIEPWERNA.
```

2. Protein Expression and Purification Based on Nickel Affinity Chromatography Followed by Anion Exchange Chromatography.

Unless mentioned otherwise, E. coli BL21(DE3) harboring pET19-TdTcys was grown in LB (Miller) with 100 μg/mL carbenicillin while shaking at 200 RPM. An overnight culture was diluted 1/60 into 400 mL LB in a 2 L flask without baffles and grown at 37° C. until an $OD_{600}$ of 0.40-0.45 was reached. The flasks were then cooled down to RT for 45 min without shaking and then shaken at 15° C. for 45 min. Protein expression was induced with IPTG (final conc. 1 mM) and cells were grown overnight at 15° C. and harvested by centrifugation. All protein purification steps were performed at 4° C. Cells were lysed in Buffer A (20 mM Tris-HCl, pH 8.3, 0.5 M NaCl)+5 mM imidazole and the lysate was subjected to nickel affinity chromatography (HisTrap FF 5 mL, GE Healthcare) with an imidazole gradient (Buffer A+5 mM imidazole to Buffer A+500 mM imidazole). Fractions with sufficient purity were pooled, diluted 1:40 into 20 mM Tris-HCl, pH 8.3 and subjected to anion-exchange chromatography (HiTrap Q HP 5 mL, GE Healthcare) in 20 mM Tris-HCl using a gradient of 0 to 1 M NaCl. The protein eluted at 200 mM NaCl. The protein was stored at −20° C. after the addition of 50% glycerol.

3. Preparation of TdT-dNTP Conjugates.

Propargylamino-dNTPs (pa-dNTPs) were coupled to the photocleavable NHS carbonate-maleimide crosslinker BP-23354 (FIG. 4A) in a 35 μL reaction containing 3.3 mM of the respective pa-dNTP, 6.6 mM linker, 66 mM $KH_2PO_4$ at pH 7.5 and 33 mM NaCl, for 1 h at RT with gentle vortexing. The reaction was split up into 7.5 μL aliquots, triturated with ethyl acetate (~2 mL) and centrifuged at 15,000 g to pellet the linker-nucleotides. The supernatant was removed and the pellets were dried in a speedvac at RT for 8 min. The pellets were resuspended in 2.5 μL of water and the linker-nucleotides were added to 20 μL of TdTcys protein prepared as described above plus 2.5 μL of pH 6.5 buffer (2 M $KH_2PO_4$, 1 M NaCl) and incubated for 1 h at RT. TdTcys-linker-dNTP conjugates (also referred to as TdT-dNTP conjugates) were then purified using amylose resin (NEB) in 0.8 mL spin columns (Pierce). All reagents and buffers were precooled on ice. The 25 μL TdTcys linker-nucleotide conjugation reaction was diluted into 400 μL Buffer B (200 mM $KH_2PO_4$ pH 7.5, 100 mM NaCl) and split across two purification columns, each containing 250 μL amylose resin in Buffer B. After 10 min of protein binding with gentle vortexing, the column was washed twice with Buffer B, and then twice with 1×NEB TdT reaction buffer (50 mM potassium acetate, 20 mM Tris-acetate, 10 mM magnesium acetate, pH 7.9). Washing was performed by adding 500 μL buffer to the column, incubating for 1 min on a shaker block to mix resin and buffer (800 RPM), followed by centrifugation at 50 g for 1 min. Elution was performed by twice resuspending the resin in 150 μL TdT reaction buffer+10 mM maltose with shaking for 5 minutes followed by centrifugation. The eluates were combined and concentrated in 30 kDa MWCO columns, diluted 1:10 with TdT reaction buffer, and then concentrated to ~2.5 μg/μL.

Analogs of the four nucleotides dATP, dCTP, dGTP, and dTTP were separately coupled to the photocleavable crosslinker and tethered to TdT. The different polymerase-nucleotide conjugates were purified using amylose affinity chromatography.

4. Capillary Electrophoresis Analysis and Ladder Generation.

Capillary electrophoresis (CE) analysis throughout Example 2 was run on an ABI 3730×1 DNA Analyzer. GeneScan Liz600 v1.0 (Thermo) was added to all samples for use as internal size standards. Ladders (size standards) for 5'-FAM labeled 60-mer dT-oligonucleotide (5'-FAM-dT (60)) extension products were generated by the incorporation of free pa-dNTPs with TdT. Reactions contained 100 nM 5'-FAM-dT(60), 100 μM of one type of pa-dNTP, 1×RBC and either 0.05 U/μL or 0.03 U/μL NEB TdT. Reactions were performed at 37° C. Aliquots were taken after 2, 5 and 10 min and quenched with EDTA to a final concentration of 33.3 mM. Quenched samples were then acetylated using NHS-acetate, purified Oligo Clean & Concentrator kit ("OCC", Zymo Research) and analyzed by capillary electrophoresis. Samples with detectable peaks for 5'-FAM-dT(60) as well as the +1 and +2 pa-dNTP extension products were chosen as size standards (ladders).

5. Demonstration of Two Reaction Cycles on PAGE and Capillary Electrophoresis.

Throughout the experiment, primer extension reactions were performed for 2 min at 37° C. and quenched by the addition of an equal volume of 200 mM EDTA. All reactions contained 50 nM 5'-FAM-dT(60), TdTcys(-linker)/TdT-dCTP at 0.25 mg/mL and 1×RBC (1×NEB TdT reaction buffer, 0.25 mM cobalt). Light induced cleavage of the linker was performed using a Benchtop 2UV Transilluminator (UVP, LLC) on the 365 nm setting for 1 h on ice. Measured irradiance was approximately 5 mW/cm$^2$. Two cycle experiment: a reaction containing TdT-dCTP conjugate and 5'-FAM-dT(60) was performed and the product was cleaved with 365 nm light. The oligo was then purified (Zymo OCC), and subjected to another reaction with TdT-dCTP, again followed by a light cleavage step. Aliquots were taken after both extension reactions (for PAGE) and after both light cleavage reactions (for PAGE and CE). For the control experiment ("control unlinked"), TdT-dCTP conjugate was cleaved by irradiation with 365 nm light for 1 h on ice to generate an equimolar mix of unlinked TdTcys(-linker)+pa-dCTP. The products were then reacted with 5'-FAM-dT(60). Aliquots for PAGE and CE were taken after quenching the reaction with EDTA. Sample preparation: all CE samples were acetylated using 20 mM NHS-acetate in bicarbonate buffer prior to analysis. Samples were combined with SDS loading dye and analyzed by PAGE, the gel was imaged for green fluorescence (of the 5'FAM-labeled primer) and, after staining with Lumitein UV (Biotium), imaged for red fluorescence (total protein).

Exposure of a 5' FAM-labeled oligonucleotide primer to TdT-dCTP conjugate resulted in a covalent complex visible on SDS-PAGE containing both the DNA primer and the protein (FIG. 9A). Irradiation of the complex with 365 nm UV light cleaved the linker and thereby dissociated the complex, releasing a primer that had been predominantly extended by a single scarred dCMP nucleotide (FIG. 9B). This product was exposed to fresh TdT-dCTP, and it again formed a primer-TdT complex, which again was dissociated by UV irradiation, releasing a primer that had now been extended by two nucleotides. In contrast, no primer-TdT complex formation was observed in a control reaction in TdT-dCTP was irradiated prior to addition of the DNA primer (FIG. 9A); instead, the control reaction produced a variety of primer extension products (FIG. 9B) consistent with TdT-catalyzed incorporation of free nucleotides.

These data show that the process of extending a primer by one nucleotide using a polymerase-nucleotide conjugate can be repeated to elongate a primer by a defined sequence.

6. Rapid Single Nucleotide Incorporation by TdT-dCTP, TdT-dGTP, TdT-dTTP, and TdT-dATP.

Oligonucleotide extension yield by 1.5 mg/mL TdT-dNTP conjugate was measured at 8, 15, and 120 seconds. Reactions were performed at 37° C. by adding 4.5 μL of TdT-dNTP conjugate (2 mg/mL) to 1.5 μL 5'-FAM-dT(60) (100 nM, final 25 nM), both in 1×RBC. After rapid mixing, 4.5 μL of the reaction were quenched in 18 μL QS (94% HiDi formamide, 10 mM EDTA) after 8 or 15 sec. The remaining reaction volume was quenched with 6 μL QS after 2 min. All samples were irradiated at 365 nm on a Benchtop 2UV Transilluminator (UVP, LLC) for 30 min to cleave the linker. Cleavage products were diluted with wash buffer (0.67 M NaH$_2$PO$_4$, 0.67 M NaCl, 0.17 M EDTA, pH 8) and captured onto DynaBeads M-280 StreptAvidin (Thermo) saturated with a 5' biotinyl dA(60) oligo, washed, acetylated using 100 mM NHS-acetate in bicarbonate buffer, and eluted with 75% deionized formamide for CE.

Figure 10:
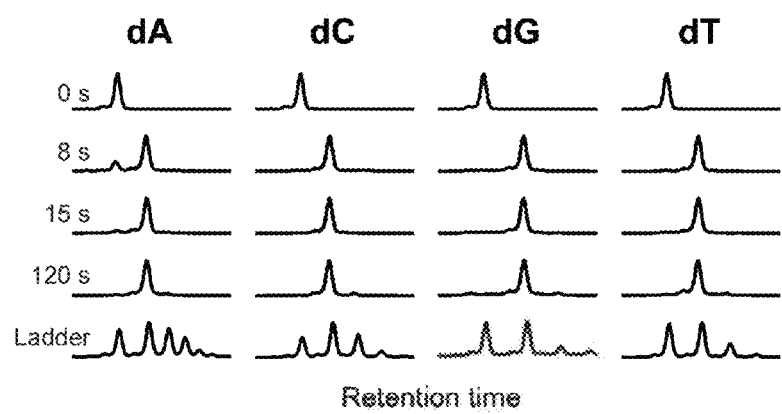
FIG. 10. Capillary electropherograms of reaction time courses for the extension of a 25 nM DNA primer by 16 µM TdT-dATP, -dCTP, -dGTP, and -dTTP conjugates, followed by photolysis.

The CE data in FIG. 10 show that the primer was transformed into the singly-extended complex in less than 20 sec of incubation with TdT-dCTP, TdT-dGTP, TdT-dTTP, and TdT-dATP. These results demonstrate that polymerase-nucleotide conjugates can elongate a primer by one nucleotide rapidly and with excellent yield.

7. Cyclic Synthesis of a Defined DNA Sequence.

Four iterations of nucleic acid extension and deprotection were performed using TdT-dNTP conjugates at 0.25 mg/mL. Extension reactions were performed with 2 min incubations at 37° C. in 1×RBC and were quenched by the addition of an equal volume of quenching buffer (250 mM EDTA, 500 mM NaCl). Cleavage of the linker was performed by irradiation at 365 nm. The first extension reaction contained TdT-dCTP and 50 nM oligo C1 (/5Phos/UT-GAAGAGCGAGAGTGAGTGA/iFluorT/CATTAAA-GACGTGGGCCTGGAttt (SEQ ID NO: 3) where /5Phos/ refers to a 5' phosphorylation, /iFluorT/ refers to a dT nucleotide base-modified with fluorescein). After photolysis, the extension product was purified (Zymo OCC), and the recovered DNA was subjected to the next extension step with TdT-dTTP. Two more cycles were performed with TdT-dATP and subsequently with TdT-dGTP, and the ultimate product was T-tailed using TdT and free dTTP+ddTTP at a ratio of 100:1. The tailed product was then PCR-amplified using HotStart Taq (NEB) with primers C2 (GTGCCGTGAGACCTGGCTCCTGACGATATGGA-TaagcttTGAAGA GCGAGAGTGAGTGA; SEQ ID NO:4) and C3 (AAAAgaatt-cAAAAAAAAAAAAAAAAAAAAAAAAAAAA AAAAAAAAAAAAAAAAAA; SEQ ID NO:5) (PCR program: Initial cycle of 98° C. for 2 min, 49° C. for 20 sec, 68° C. for 5 min, then 30 cycles of three step protocol: 98° C. for 30 sec, 49° C. for 20 sec, 68° C. for 30 sec). The PCR product was inserted into the pUC19 plasmid using EcoRI and HindIII sites that were introduced by the PCR primers. The plasmid was transformed into DH10B cells and the plasmids of single colonies were extracted after overnight growth in LB and sequenced.

Figure 11A:
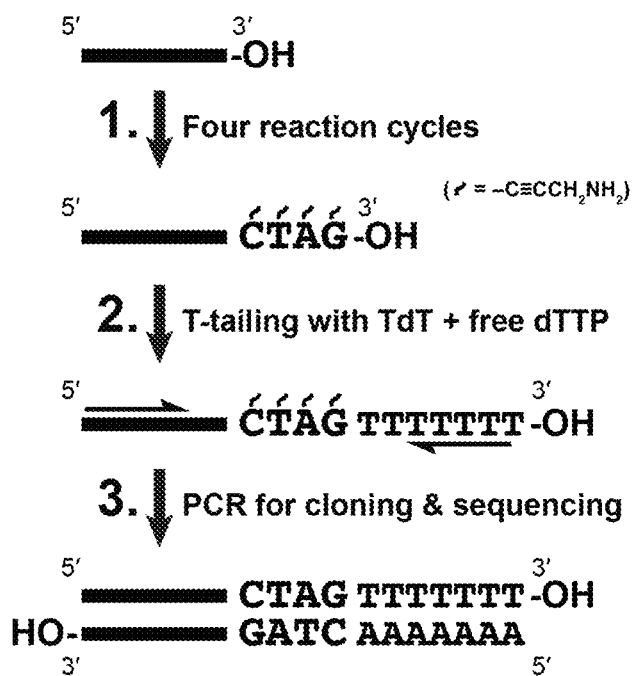
FIGS. 11A-11B. Demonstration of synthesis of a 4-mer (5'-CTAG-3').
Figure 11B:

As described in detail above, four iterations of the reaction cycle were performed on a starter DNA molecule, the tailed products were PCR-amplified, and the amplicon was cloned for sequencing as depicted in FIG. 11A. Of 35 clones sequenced, 31 (89%) contained the complete 5'-CTAG-3' sequence (FIG. 11B), implying an average stepwise yield of 97%. These data show that polymerase-nucleotide conjugates can be used in a cyclic process to write a defined sequence of DNA with excellent stepwise yield.

Example 3

Incorporation of Free dNTPs into a Primer Already Tethered to a Polymerase

Figure 12:
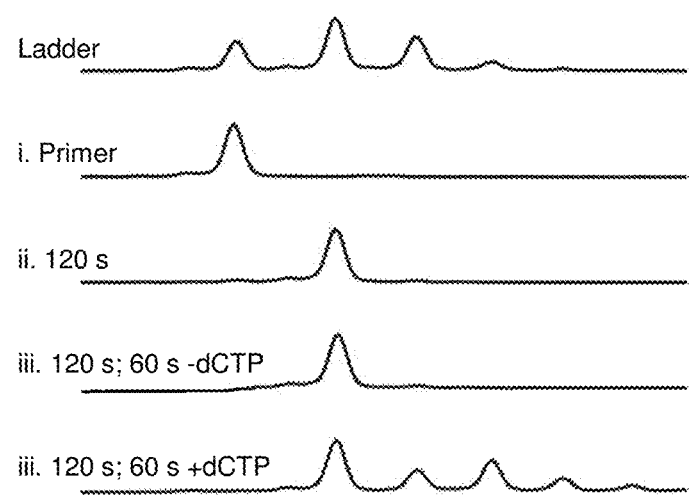
FIG. 12. Demonstration of free nucleotide incorporation into a primer that is tethered to a polymerase via its incorporated tethered nucleotide, analyzed by CE.

The experiment was performed using TdT-dCTP conjugates as prepared in Example 2. Capillary electrophoresis analysis was also performed as described in Example 2, and the same oligonucleotide ladder was used as size reference. 5'-FAM-dT$_{60}$ (50 nM) was incubated with TdT-dCTP (0.25 mg/mL) for 120 sec at 37° C. in 1×RBC to yield a primer-polymerase complex and the reaction was split into aliquots. One aliquot was quenched by the addition EDTA to a final concentration of 100 mM. Another aliquot was diluted 10-fold with 1×RBC. Another aliquot was diluted 10-fold with 1×RBC containing free pa-dCTP to a final concentration of 500 µM pa-dCTP. After incubation at 37° C. for another 60 sec, both reactions were quenched by the addition of EDTA to a final concentration of 100 mM. Light induced cleavage of the linker for all samples was performed using a Benchtop 2UV Transilluminator (UVP, LLC) on the 365 nm setting for 1 h on ice. The samples were acetylated using 20 mM NHS-acetate in bicarbonate buffer, purified and analyzed by CE. During the initial incubation of the primer with TdT-dCTP, a primer-polymerase complex forms, as indicated by the extension of the primer by a single nucleotide observed by CE analysis (FIG. 12). In the reaction allowed to proceed for another 60 sec, no further extensions of the primer are detected. However, in the reaction allowed to proceed for another 60 sec with free nucleoside triphosphates (pa-dCTP) added, further extensions of the tethered primer were observed.

These results show that a nucleic acid-polymerase complex that is formed upon tethered incorporation of a nucleoside triphosphate by a polymerase-nucleotide conjugate may still be able to incorporate free nucleoside triphosphates.

Example 4

Conversion of a "Scarred" Polynucleotide into Natural DNA

Fluorescent primers were prepared by labeling amine-containing oligos with 4.5 mM fluorophore NHS ester in sodium bicarbonate buffer followed by OCC. A 639 nt DNA product containing deoxyuridine bases was obtained by 35 cycles of PCR using Phusion U (Thermo) following the manufacturer's instructions (two step protocol: 98° C. denaturation for 10 sec, 72° C. annealing/extension for 1 min) from the plasmid template pMal-c5×(NEB) using primers PA1 (/5Phos/cattaaagacgtgggcgtgga; SEQ ID NO:6) and PA2 (t*t*t/iUniAmM/tgtgaaatccttccctcgatcc; SEQ ID NO:7). Primer PA1 is 5' phosphorylated; primer PA2 contains an internal amino group (/iUniAmM/) labeled with Cy3 NHS (GE Healtcare) and begins with two phosphorothioate linkages (*) to render it exonuclease-resistant. The PCR product was purified from a 1% TAE-agarose gel and ~6.7 µg of product was digested with 5 U of Lambda exonuclease (NEB) in a 100 µL reaction for 20 min at 37° C. to isolate the Cy3-labeled strand. Digestion products were purified by OCC and then hybridized at ~1 µM with equimolar 5'FAM-labeled primer PA3 (/5AmMC6/ CAACACACCACCCACCCAACcgcagatgtccgctttctgg (SEQ ID NO:14); /5AmMC6/ refers to an aminohexyl modification of a 5' phosphate) in 1×CutSmart buffer (NEB) by heating to 85° C. and cooling to 25° C. at 1° C./min. N-acetyl propargylamino dNTPs were prepared by acetylating 13 mM propargylamino dNTPs with 25 mM NHS acetate in 100 mM sodium bicarbonate buffer and quenched with glycine to 25 mM final. The primer was then elongated using 7.5 U of Klenow(exo-) (NEB) in 30 µL reactions at 37° C. with 200 µM (each) N-acetyl propargylamino dNTPs (reaction ii) or without any dNTPs (reaction i). After 1 hour, 3 µL of 2.5 mM (each) ddNTPs (Affymetrix) were added to both reactions for an additional 15 min incubation followed by inactivation of the polymerase by heating to 75° C. for 20 minutes. The products were then immediately digested in 50 µL reactions using 5 U of USER Enzyme (NEB) at 37° C. for 1 hour to remove the dU-containing ssDNA template. Digestion products were purified by OCC and propargylamino dNTP-dependent elongation of the 5'FAM-labeled primer and USER digestion of the Cy3-labeled template were confirmed by CE. Both products were then used as templates for complementary DNA synthesis ("reading") by 5 U of Taq (Thermo) using 200 µM (each) natural dNTPs and 200 nM of the 5' Cy3-labeled primer PA4 (/5AmMC6/ CGACTCACCTCACGTCCTCAtgtgaaatccttccctcgatcc; SEQ ID NO:8) in a 20 µL reaction by heating to 95° C. for 2 min and then incubating at 45° C. After 30 minutes, 1 µL of 2.5 mM (each) ddNTPs was added to both reactions for an additional 15 min incubation, and the DNA products were purified. Equal volumes of both reading products were then analyzed by qPCR on a CFX96 instrument (Bio-Rad), using Phusion HS II (Thermo) with 1×EvaGreen (Biotium) and primers PA5 (ttttGAATTCCAACACACCACCCACC-CAAC; SEQ ID NO:9) and PA6 (ttttAAGCTTCGACT-CACCTCACGTCCTCA; SEQ ID NO:10) for 30 cycles of 98° C. for 5 sec, 67° C. for 15 sec, and 72° C. for 30 sec. qPCR products from reaction ii were inserted into a pUC19 plasmid using EcoRI and HindIII sites introduced by the PCR primers and 81 clones were sequenced as described above.

Figure 13A:
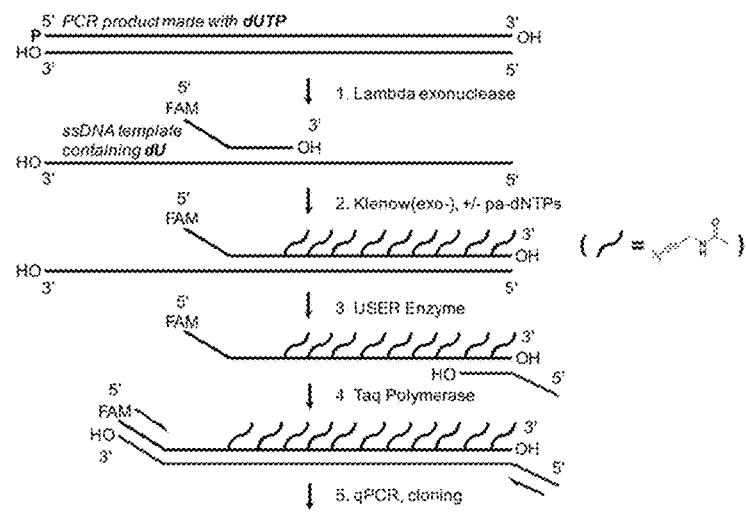
FIGS. 13A-13C. Experimental setup to demonstrate that scarred DNA can serve as a template for accurate complementary DNA synthesis.
Figure 13B:
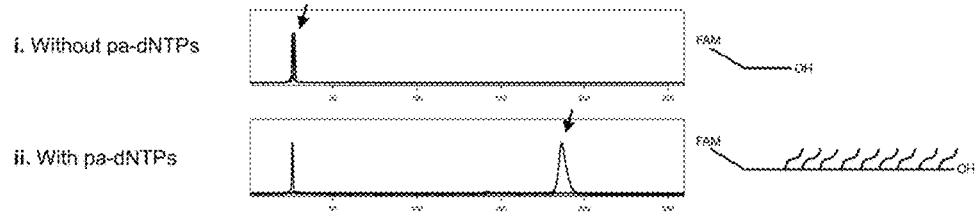
Figure 13C:
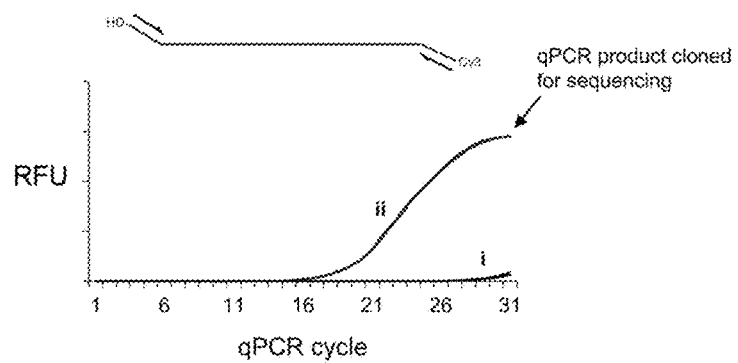

The dNTP analogs used in this example contain a propargylamino group extending from the nucleobase (5 position of pyrimidines, 7 position of 7-deazapurines) which is the same moiety the polymerase-nucleotide conjugates from Example 2 leave as a scar. The propargylamino moiety was further derivitized by N-acetylation. To demonstrate that DNA comprising scarred bases as produced in Example 2 can serve as template for accurate synthesis of complementary DNA by a template-dependent polymerase using natural dNTPs, in this example a DNA molecule containing 141 sequential 3-acetamidopropynyl (i.e. N-acetylated propargylamino) nucleotides was prepared. This DNA product was isolated and used as template for PCR (FIGS. 13A-13C). The PCR product was inserted into a plasmid, cloned into $E.$ $coli$ and 81 colonies were sequenced. 5 errors were found, implying an error rate for the synthesis of natural DNA from the 3-acetamidopropynyl modified template of approximately $6 \times 10^{-4}$/nt.

This data shows that scarred nucleic acids (in this case a polynucleotide harboring a moiety derivable from the propargylamino scar from Example 2) can be PCR-amplified with high fidelity, thereby generating natural DNA that can be used in biological applications.

Example 5. Synthesis of a 10-Mer

Ten extensions of the 3' overhang of a double-stranded DNA molecule were performed using TdT-dNTP conjugates as prepared in Example 2. The double stranded DNA used as initial substrate was prepared from a ~350 bp PCR product derived from the pET19b plasmid using Phusion Polymerase (Thermo) following the manufacturer's instructions (two step protocol: 98° C. for 10 sec, 72° C. for 45 sec) with the primers T1 (/5Phos/GCAGC-CAACTCAGCTTCTGCAGGGGCTTTGTTAGCAGCCG-GATCCTC; SEQ ID NO:11) and T2 (AAACAAGCGCT-CATGAGCCAGAAATCTGGAGCCCGATCTTCCCCAT CGG; SEQ ID NO:12). The PCR product was digested with PstI to generate a 3' overhang on one side, that was then tailed with ddTTP using TdT to prevent elongation of the generated 3' overhang. After tailing, the DNA was digested with BstXI to generate a 3' overhang on the other end of the amplicon to enable extensions by polymerase-nucleotide conjugates. The digestion product was isolated by 2% agarose gel electrophoresis and purified to yield the initial substrate for extensions by polymerase-nucleotide conjugates.

The extension reactions were performed for 90 sec at 37° C. in 1×RBC with 1 mg/mL of the respective polymerase-nucleotide conjugate and were quenched by the addition of an equal volume of quenching buffer (250 mM EDTA, 500 mM NaCl). Cleavage of the linker was performed by irradiation at 365 nm. The first extension reaction contained ~40 nM of the initial substrate. After each cleavage step, the DNA products were purified (Zymo OCC), and the recovered DNA was subjected to the next extension step. The following conjugates were used in the extension steps: 1) TdT-dCTP, 2) TdT-dTTP, 3) TdT-dATP, 4) TdT-dCTP, 5) TdT-dTTP, 6) TdT-dGTP, 7) TdT-dATP, 8) TdT-dCTP, 9) TdT-dTTP, 10) TdT-dGTP. The ten-cycle product was T-tailed using TdT and free dTTP+ddTTP at a ratio of 100:1 and acetylated using 20 mM NHS-acetate in bicarbonate buffer. The tailed product was then PCR-amplified using HotStart Taq (NEB) with primers C3 and C4 (GTGCCGT-GAGACCTGGCTCCTGACGAGGAtaagcttCTATAGT-GAGTCGT ATTAATTTCG; SEQ ID NO:13) (PCR program: Initial cycle of 98° C. for 2 min, 49° C. for 20 sec, 68° C. for 12 min, then 30 cycles of three step protocol: 98° C. for 30 sec, 49° C. for 20 sec, 68° C. for 30 sec). The PCR product was inserted into pUC19 using EcoRI and HindIII sites that were introduced by the PCR primers. The plasmids were transformed into DH10B cells and the plasmids of single colonies were extracted after overnight growth in LB and sequenced.

Figure 14A:
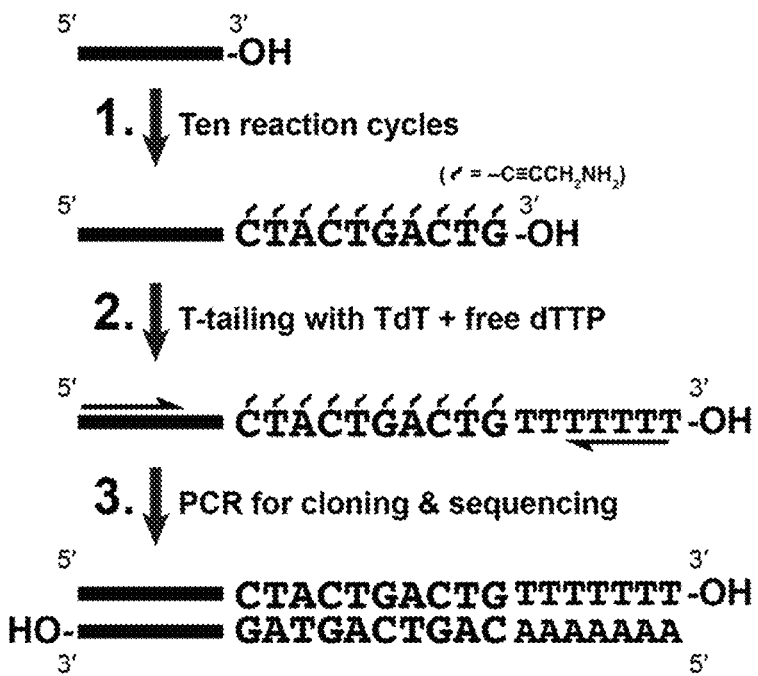
FIGS. 14A-14B. Demonstration of synthesis of a 10-mer (5'-CTACTGACTG-3') (SEQ ID NO:18).
Figure 14B:

As described in more detail above, a double stranded DNA template was elongated by 10 cycles using polymerase-nucleotide conjugates, the synthesis product was amplified and cloned for sequencing (FIG. 14A). Of 32 clones sequenced, 13 (41%) contained the complete 5'-CTACTGACTG-3' sequence (FIG. 14B), implying an average stepwise yield of 91%.

This result demonstrates that the cyclic process of DNA extension can be repeated many times to write nucleic acid molecules of the desired sequence and length.

The invention claimed is:

1. A conjugate comprising a nucleotide, a linker, and a template-independent polymerase capable of catalyzing the covalent addition of the nucleotide onto the 3' end of a nucleic acid, wherein the linker tethers the nucleotide to the template-independent polymerase.

2. The conjugate of claim 1, wherein the linker is selectively cleavable.

3. The conjugate of claim 2, wherein cleavage of the linker releases the template-independent polymerase from the nucleotide.

4. The conjugate of claim 3, wherein cleavage of the linker leaves a scar on the nucleobase of the nucleotide, and wherein the scar comprises a part of the linker retained on the nucleobase after cleavage of the linker.

5. The conjugate of claim 4, wherein the scar on the nucleobase is selectively removable.

6. The conjugate of claim 5, wherein removal of the scar leaves a naturally occurring nucleobase.

7. The conjugate of claim 6, wherein the scar is selectively removable by chemical cleavage, enzymatic cleavage, or photocleavage.

8. The conjugate of claim 3, wherein cleavage of the linker does not produce a scar on the nucleotide.

9. The conjugate of claim 1, wherein the nucleotide is a nucleoside triphosphate.

10. The conjugate of claim 1, wherein the nucleotide comprises a nucleobase selected from the group consisting of adenine, cytosine, guanine, thymine, and uracil.

11. The conjugate of claim 1, wherein the linker is bound to the nucleotide at the nucleobase, sugar, or the α-phosphate of the nucleotide.

12. The conjugate of claim 1, wherein the polynucleotide is tethered to a solid support.

13. The conjugate of claim 1, wherein the template-independent polymerase is engineered to comprise a predetermined target site to which the nucleotide is specifically tethered.

14. The conjugate of claim 13, wherein the predetermined target site comprises a modified amino acid.

15. The conjugate of claim 14, wherein the modified amino acid comprises p-propargyloxyphenylalanine or p-azidophenylalanine.

16. The conjugate of claim 1, wherein the template-independent polymerase comprises one or more cysteine substitutions.

17. The conjugate of claim 1, wherein the linker is specifically attached at a predetermined target site that is a cysteine residue of the template-independent polymerase; a lysine residue of the template-independent polymerase; an unnatural amino acid residue of the template-independent polymerase; a peptide tag of the template-independent polymerase; a labeling domain fused to the template-independent polymerase; or an aldehyde specifically generated within the template-independent polymerase.

18. The conjugate of claim 1, wherein the linker is specifically attached at a predetermined target site that is a cysteine residue of the template-independent polymerase, wherein the linker is attached via a sulfhydryl-reactive chemistry.

19. The conjugate of claim 1, wherein the template-independent polymerase is a terminal deoxynucleotidyl transferase (TdT), or a variant thereof.

20. The conjugate of claim 1, further comprising a fluorescent label.

21. The conjugate of claim 1, wherein the linker has a length of 4-100 Å.

22. The conjugate of claim 1, wherein the linker comprises a chemically-cleavable linkage, an enzyme-cleavable linkage, or a photo-cleavable linkage.

23. The conjugate of claim 22, wherein the chemically-cleavable linkage is selected from the group consisting of: a base-cleavable linkage, an acid-cleavable linkage, and a nucleophile-cleavable linkage.

24. The conjugate of claim 23, wherein the base-cleavable linkage is selected from the group consisting of: an ester, a quaternary ammonium salt, and a urethane.

25. The conjugate of claim 23, wherein the acid-cleavable linkage is selected from the group consisting of: a benzyl alcohol derivative, a teicoplanin aglycone, an acetal, a thioacetal, a thioether and a sulfonyl.

26. The conjugate of claim 23, wherein the nucleophile-cleavable linkage is selected from the group consisting of: a phthalimide, an ester, and a Weinreb amide.

27. The conjugate of claim 22, wherein the chemically-cleavable linkage is selected from the group consisting of: a disulfide, a phosphorothioate, a diol, and an azobenzene.

28. The conjugate of claim 22, wherein the enzyme-cleavable linkage comprises an ester.

29. A method of nucleic acid synthesis, comprising:
providing a conjugate comprising a nucleotide, a linker, and a template-independent polymerase capable of catalyzing the covalent addition of the nucleotide onto the 3' end of a nucleic acid, wherein the linker tethers the nucleotide to the template-independent polymerase; and contacting a sample comprising the nucleic acid with the conjugate.

30. A method of synthesizing a polynucleotide having a defined sequence, comprising steps:
(a) contacting a substrate comprising a nucleic acid with a conjugate comprising nucleotide, a linker, and a template-independent polymerase capable of catalyzing the covalent addition of the nucleotide onto the 3' end of the nucleic acid, wherein the linker tethers the nucleotide to the template-independent polymerase;
(b) exposing the substrate to conditions sufficient to cleave the linker to separate the template-independent polymerase from the nucleotide; and
(c) repeating steps (a) and (b) one or more times to synthesize the polynucleotide having a defined sequence.

31. The conjugate of claim 3, wherein cleavage of the linker does not produce a scar on the nucleobase.

32. The conjugate of claim 3, wherein cleavage of the linker leaves a naturally occurring nucleobase.

* * * * *

SEQUENCE LISTING

```
<160> NUMBER OF SEQ ID NOS: 24

<210> SEQ ID NO 1
<211> LENGTH: 384
<212> TYPE: PRT
<213> ORGANISM: Tarsius syrichta

<400> SEQUENCE: 1

Met Gly His His His His His His His His Ser Ser Gly His
1               5                   10                  15

Ile Asp Asp Asp Asp Lys His Met Ser Gln Tyr Ala Cys Gln Arg Arg
            20                  25                  30

Thr Thr Leu Asn Asn His Asn Gln Ile Phe Thr Asp Ala Phe Asp Ile
        35                  40                  45

Leu Ala Glu Asn Asp Glu Phe Arg Glu Asn Glu Gly Pro Ser Leu Thr
    50                  55                  60

Phe Met Arg Ala Ala Ser Val Leu Lys Ser Leu Pro Phe Thr Ile Ile
65                  70                  75                  80

Ser Met Lys Asp Ile Glu Gly Ile Pro Asn Leu Gly Asp Arg Val Lys
                85                  90                  95

Ser Ile Ile Glu Glu Ile Ile Glu Asp Gly Glu Ser Ser Ala Val Lys
            100                 105                 110

Ala Val Leu Asn Asp Glu Arg Tyr Lys Ser Phe Lys Leu Phe Thr Ser
        115                 120                 125

Val Phe Gly Val Gly Leu Lys Thr Ser Glu Lys Trp Phe Arg Met Gly
    130                 135                 140

Phe Arg Thr Leu Ser Asn Ile Arg Ser Asp Lys Ser Leu Thr Phe Thr
```

```
            145                 150                 155                 160
        Arg Met Gln Arg Ala Gly Phe Leu Tyr Tyr Glu Asp Leu Val Ser Arg
                        165                 170                 175

Val Thr Arg Ala Glu Ala Glu Ala Val Gly Val Leu Val Lys Glu Ala
                        180                 185                 190

Val Trp Ala Ser Leu Pro Asp Ala Phe Val Thr Met Thr Gly Gly Phe
                        195                 200                 205

Arg Arg Gly Lys Lys Thr Gly His Asp Val Asp Phe Leu Ile Thr Ser
                        210                 215                 220

Pro Gly Ala Thr Glu Glu Glu Gln Gln Leu Leu His Lys Val Ile
        225                 230                 235                 240

Ser Leu Trp Glu His Lys Gly Leu Leu Leu Tyr Tyr Asp Leu Val Glu
                        245                 250                 255

Ser Thr Phe Glu Lys Leu Lys Leu Pro Ser Arg Lys Val Asp Ala Leu
                        260                 265                 270

Asp His Phe Gln Lys Cys Phe Leu Ile Leu Lys Leu His His Gln Arg
                        275                 280                 285

Val Asp Ser Asp Gln Ser Ser Trp Gln Glu Gly Lys Thr Trp Lys Ala
                        290                 295                 300

Ile Arg Val Asp Leu Val Val Cys Pro Tyr Glu Arg Arg Ala Phe Ala
        305                 310                 315                 320

Leu Leu Gly Trp Thr Gly Ser Arg Gln Phe Glu Arg Asp Leu Arg Arg
                        325                 330                 335

Tyr Ala Thr His Glu Arg Lys Met Ile Ile Asp Asn His Ala Leu Tyr
                        340                 345                 350

Asp Lys Thr Lys Arg Ile Phe Leu Glu Ala Glu Ser Glu Glu Glu Ile
                        355                 360                 365

Phe Ala His Leu Gly Leu Asp Tyr Ile Glu Pro Trp Glu Arg Asn Ala
                        370                 375                 380

<210> SEQ ID NO 2
        <211> LENGTH: 807
        <212> TYPE: PRT
        <213> ORGANISM: Artificial Sequence
        <220> FEATURE:
        <223> OTHER INFORMATION: Synthetic sequence

<400> SEQUENCE: 2

Met Gly His His His His His His His His Ser Ser Gly His
        1               5                   10                  15

Ile Asp Asp Asp Lys His Met Met Lys Ile Glu Glu Gly Lys Leu
                        20                  25                  30

Val Ile Trp Ile Asn Gly Asp Lys Gly Tyr Asn Gly Leu Ala Glu Val
                        35                  40                  45

Gly Lys Lys Phe Glu Lys Asp Thr Gly Ile Lys Val Thr Val Glu His
                50                  55                  60

Pro Asp Lys Leu Glu Glu Lys Phe Pro Gln Val Ala Ala Thr Gly Asp
        65                  70                  75                  80

Gly Pro Asp Ile Ile Phe Trp Ala His Asp Arg Phe Gly Gly Tyr Ala
                        85                  90                  95

Gln Ser Gly Leu Leu Ala Glu Ile Thr Pro Asp Lys Ala Phe Gln Asp
                        100                 105                 110

Lys Leu Tyr Pro Phe Thr Trp Asp Ala Val Arg Tyr Asn Gly Lys Leu
                        115                 120                 125

Ile Ala Tyr Pro Ile Ala Val Glu Ala Leu Ser Leu Ile Tyr Asn Lys
```

```
              130                 135                 140
Asp Leu Leu Pro Asn Pro Pro Lys Thr Trp Glu Glu Ile Pro Ala Leu
145                 150                 155                 160

Asp Lys Glu Leu Lys Ala Lys Gly Lys Ser Ala Leu Met Phe Asn Leu
                165                 170                 175

Gln Glu Pro Tyr Phe Thr Trp Pro Leu Ile Ala Ala Asp Gly Gly Tyr
            180                 185                 190

Ala Phe Lys Tyr Glu Asn Gly Lys Tyr Asp Ile Lys Asp Val Gly Val
        195                 200                 205

Asp Asn Ala Gly Ala Lys Ala Gly Leu Thr Phe Leu Val Asp Leu Ile
    210                 215                 220

Lys Asn Lys His Met Asn Ala Asp Thr Asp Tyr Ser Ile Ala Glu Ala
225                 230                 235                 240

Ala Phe Asn Lys Gly Glu Thr Ala Met Thr Ile Asn Gly Pro Trp Ala
                245                 250                 255

Trp Ser Asn Ile Asp Thr Ser Lys Val Asn Tyr Gly Val Thr Val Leu
            260                 265                 270

Pro Thr Phe Lys Gly Gln Pro Ser Lys Pro Phe Val Gly Val Leu Ser
        275                 280                 285

Ala Gly Ile Asn Ala Ala Ser Pro Asn Lys Glu Leu Ala Lys Glu Phe
    290                 295                 300

Leu Glu Asn Tyr Leu Leu Thr Asp Glu Gly Leu Glu Ala Val Asn Lys
305                 310                 315                 320

Asp Lys Pro Leu Gly Ala Val Ala Leu Lys Ser Tyr Glu Glu Glu Leu
                325                 330                 335

Val Lys Asp Pro Arg Ile Ala Ala Thr Met Glu Asn Ala Gln Lys Gly
            340                 345                 350

Glu Ile Met Pro Asn Ile Pro Gln Met Ser Ala Phe Trp Tyr Ala Val
        355                 360                 365

Arg Thr Ala Val Ile Asn Ala Ala Ser Gly Arg Gln Thr Val Asp Glu
    370                 375                 380

Ala Leu Lys Asp Ala Gln Thr Asn Ser Ser Ser Asn Asn Asn Asn Asn
385                 390                 395                 400

Asn Asn Asn Asn Asn Leu Gly Ile Glu Gly Arg Ile Ser His Met Ser
                405                 410                 415

Met Gly Gly Arg Asp Ile Val Asp Gly Ser Glu Phe Ser Pro Ser Pro
            420                 425                 430

Val Pro Gly Ser Gln Asn Val Pro Ala Pro Ala Val Lys Lys Ile Ser
        435                 440                 445

Gln Tyr Ala Cys Gln Arg Arg Thr Thr Leu Asn Asn Tyr Asn Gln Leu
    450                 455                 460

Phe Thr Asp Ala Leu Asp Ile Leu Ala Glu Asn Asp Glu Leu Arg Glu
465                 470                 475                 480

Asn Glu Gly Ser Ala Leu Ala Phe Met Arg Ala Ser Ser Val Leu Lys
                485                 490                 495

Ser Leu Pro Phe Pro Ile Thr Ser Met Lys Asp Thr Glu Gly Ile Pro
            500                 505                 510

Ser Leu Gly Asp Lys Val Lys Ser Ile Ile Glu Gly Ile Ile Glu Asp
        515                 520                 525

Gly Glu Ser Ser Glu Ala Lys Ala Val Leu Asn Asp Glu Arg Tyr Lys
    530                 535                 540

Ser Phe Lys Leu Phe Thr Ser Val Phe Gly Val Gly Leu Lys Thr Ala
545                 550                 555                 560
```

```
Glu Lys Trp Phe Arg Met Gly Phe Arg Thr Leu Ser Lys Ile Gln Ser
                565                 570                 575
Asp Lys Ser Leu Arg Phe Thr Gln Met Gln Lys Ala Gly Phe Leu Tyr
            580                 585                 590
Tyr Glu Asp Leu Val Ser Cys Val Asn Arg Pro Glu Ala Glu Ala Val
        595                 600                 605
Ser Met Leu Val Lys Glu Ala Val Val Thr Phe Leu Pro Asp Ala Leu
    610                 615                 620
Val Thr Met Thr Gly Gly Phe Arg Arg Gly Lys Met Thr Gly His Asp
625                 630                 635                 640
Val Asp Phe Leu Ile Thr Ser Pro Glu Ala Thr Glu Asp Glu Glu Gln
                645                 650                 655
Gln Leu Leu His Lys Val Thr Asp Phe Trp Lys Gln Gln Gly Leu Leu
            660                 665                 670
Leu Tyr Ala Asp Ile Leu Glu Ser Thr Phe Glu Lys Phe Lys Gln Pro
        675                 680                 685
Ser Arg Lys Val Asp Ala Leu Asp His Phe Gln Lys Cys Phe Leu Ile
    690                 695                 700
Leu Lys Leu Asp His Gly Arg Val His Ser Glu Lys Ser Gly Gln Gln
705                 710                 715                 720
Glu Gly Lys Gly Trp Lys Ala Ile Arg Val Asp Leu Val Met Ser Pro
                725                 730                 735
Tyr Asp Arg Arg Ala Phe Ala Leu Leu Gly Trp Thr Gly Ser Arg Gln
            740                 745                 750
Phe Glu Arg Asp Leu Arg Arg Tyr Ala Thr His Glu Arg Lys Met Met
        755                 760                 765
Leu Asp Asn His Ala Leu Tyr Asp Arg Thr Lys Arg Val Phe Leu Glu
    770                 775                 780
Ala Glu Ser Glu Glu Glu Ile Phe Ala His Leu Gly Leu Asp Tyr Ile
785                 790                 795                 800
Glu Pro Trp Glu Arg Asn Ala
                805

<210> SEQ ID NO 3
<211> LENGTH: 46
<212> TYPE: DNA
<213> ORGANISM: Artificial Sequence
<220> FEATURE:
<223> OTHER INFORMATION: Syntthetic sequence
<220> FEATURE:
<221> NAME/KEY: Misc_feature
<222> LOCATION: (1)..(1)
<223> OTHER INFORMATION: 5' phosphorylation at the 5' end
<220> FEATURE:
<221> NAME/KEY: Misc_feature
<222> LOCATION: (1)..(1)
<223> OTHER INFORMATION: n is a uracil
<220> FEATURE:
<221> NAME/KEY: Misc_feature
<222> LOCATION: (22)..(22)
<223> OTHER INFORMATION: n is a deoxythymidine nucleotide base modified
      with fluorescein

<400> SEQUENCE: 3
ntgaagagcg agagtgagtg ancattaaag acgtgggcct ggattt                    46

<210> SEQ ID NO 4
<211> LENGTH: 59
<212> TYPE: DNA
<213> ORGANISM: Artificial Sequence
```

```
<220> FEATURE:
<223> OTHER INFORMATION: Synthetic sequence

<400> SEQUENCE: 4
gtgccgtgag acctggctcc tgacgatatg gataagcttt gaagagcgag agtgagtga      59

<210> SEQ ID NO 5
<211> LENGTH: 56
<212> TYPE: DNA
<213> ORGANISM: Artificial Sequence
<220> FEATURE:
<223> OTHER INFORMATION: Syntthetic sequence

<400> SEQUENCE: 5
aaaagaattc aaaaaaaaaa aaaaaaaaaa aaaaaaaaaa aaaaaaaaaa aaaaaa         56

<210> SEQ ID NO 6
<211> LENGTH: 21
<212> TYPE: DNA
<213> ORGANISM: Artificial Sequence
<220> FEATURE:
<223> OTHER INFORMATION: Syntthetic sequence
<220> FEATURE:
<221> NAME/KEY: Misc_feature
<222> LOCATION: (1)..(1)
<223> OTHER INFORMATION: phosphorylated at the 5' end

<400> SEQUENCE: 6
cattaaagac gtgggcgtgg a                                               21

<210> SEQ ID NO 7
<211> LENGTH: 26
<212> TYPE: DNA
<213> ORGANISM: Artificial Sequence
<220> FEATURE:
<223> OTHER INFORMATION: Syntthetic sequence
<220> FEATURE:
<221> NAME/KEY: Misc_feature
<222> LOCATION: (4)..(4)
<223> OTHER INFORMATION: n is a internal amino group labeled with Cy3
      NHS

<400> SEQUENCE: 7
tttntgtgaa atccttccct cgatcc                                          26

<210> SEQ ID NO 8
<211> LENGTH: 42
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(1)
<223> OTHER INFORMATION: aminohexyl modification of a 5' phosphate at
      the 5' end

<400> SEQUENCE: 8
cgactcacct cacgtcctca tgtgaaatcc ttccctcgat cc                         42

<210> SEQ ID NO 9
<211> LENGTH: 30
<212> TYPE: DNA
<213> ORGANISM: Artificial Sequence
<220> FEATURE:
<223> OTHER INFORMATION: Syntthetic sequence

<400> SEQUENCE: 9
```
ttttgaattc caacacacca cccacccaac        30

<210> SEQ ID NO 10
<211> LENGTH: 30
<212> TYPE: DNA
<213> ORGANISM: Artificial Sequence
<220> FEATURE:
<223> OTHER INFORMATION: Syntthetic sequence

<400> SEQUENCE: 10
ttttaagctt cgactcacct cacgtcctca        30

<210> SEQ ID NO 11
<211> LENGTH: 47
<212> TYPE: DNA
<213> ORGANISM: Artificial Sequence
<220> FEATURE:
<223> OTHER INFORMATION: Syntthetic sequence
<220> FEATURE:
<221> NAME/KEY: Misc_feature
<222> LOCATION: (1)..(1)
<223> OTHER INFORMATION: 5' phosphorylation at the 5' end

<400> SEQUENCE: 11
gcagccaact cagcttctgc aggggctttg ttagcagccg gatcctc        47

<210> SEQ ID NO 12
<211> LENGTH: 49
<212> TYPE: DNA
<213> ORGANISM: Artificial Sequence
<220> FEATURE:
<223> OTHER INFORMATION: Syntthetic sequence

<400> SEQUENCE: 12
aaacaagcgc tcatgagcca gaaatctgga gcccgatctt ccccatcgg        49

<210> SEQ ID NO 13
<211> LENGTH: 60
<212> TYPE: DNA
<213> ORGANISM: Artificial Sequence
<220> FEATURE:
<223> OTHER INFORMATION: Syntthetic sequence

<400> SEQUENCE: 13
gtgccgtgag acctggctcc tgacgaggat aagcttctat agtgagtcgt attaatttcg        60

<210> SEQ ID NO 14
<211> LENGTH: 40
<212> TYPE: DNA
<213> ORGANISM: Artificial Sequence
<220> FEATURE:
<223> OTHER INFORMATION: Syntthetic sequence
<220> FEATURE:
<221> NAME/KEY: Misc_feature
<222> LOCATION: (1)..(1)
<223> OTHER INFORMATION: aminohexyl modification of a 5' phosphate at
      the 5' end

<400> SEQUENCE: 14
caacacacca cccacccaac cgcagatgtc cgctttctgg        40

<210> SEQ ID NO 15
<211> LENGTH: 11
<212> TYPE: DNA
<213> ORGANISM: Artificial Sequence
<220> FEATURE:
<223> OTHER INFORMATION: Synthetic sequence
<220> FEATURE:

```
<221> NAME/KEY: Misc_Feature
<222> LOCATION: (1)..(1)
<223> OTHER INFORMATION: linked to a -C tripple bond CCH2NH2
<220> FEATURE:
<221> NAME/KEY: Misc_Feature
<222> LOCATION: (2)..(2)
<223> OTHER INFORMATION: linked to a -C tripple bond CCH2NH2
<220> FEATURE:
<221> NAME/KEY: Misc_Feature
<222> LOCATION: (3)..(3)
<223> OTHER INFORMATION: linked to a -C tripple bond CCH2NH2
<220> FEATURE:
<221> NAME/KEY: Misc_Feature
<222> LOCATION: (4)..(4)
<223> OTHER INFORMATION: linked to a -C tripple bond CCH2NH2
<220> FEATURE:
<221> NAME/KEY: Misc_Feature
<222> LOCATION: (11)..(11)
<223> OTHER INFORMATION: OH group at the 3' end

<400> SEQUENCE: 15 ctagttttt t                                                         11

<210> SEQ ID NO 16
<211> LENGTH: 11
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (11)..(11)
<223> OTHER INFORMATION: OH group at the 3' end

<400> SEQUENCE: 16 ctagttttt t                                                         11

<210> SEQ ID NO 17
<211> LENGTH: 11
<212> TYPE: DNA
<213> ORGANISM: Artificial Sequence
<220> FEATURE:
<223> OTHER INFORMATION: Synthetic sequence

<400> SEQUENCE: 17
tttctagttt t                                                        11

<210> SEQ ID NO 18
<211> LENGTH: 10
<212> TYPE: DNA
<213> ORGANISM: Artificial Sequence
<220> FEATURE:
<223> OTHER INFORMATION: Synthetic sequence

<400> SEQUENCE: 18
ctactgactg                                                          10

<210> SEQ ID NO 19
<211> LENGTH: 10
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(1)
<223> OTHER INFORMATION: linked to a -C tripple bond CCH2NH2
<220> FEATURE:
<221> NAME/KEY: Misc_feature
<222> LOCATION: (1)..(1)
<220> FEATURE:
```

```
<221> NAME/KEY: Misc_feature
<222> LOCATION: (2)..(2)
<223> OTHER INFORMATION: linked to a -C tripple bond CCH2NH2
<220> FEATURE:
<221> NAME/KEY: Misc_feature
<222> LOCATION: (3)..(3)
<223> OTHER INFORMATION: linked to a -C tripple bond CCH2NH2
<220> FEATURE:
<221> NAME/KEY: Misc_feature
<222> LOCATION: (4)..(4)
<223> OTHER INFORMATION: linked to a -C tripple bond CCH2NH2
<220> FEATURE:
<221> NAME/KEY: Misc_feature
<222> LOCATION: (5)..(5)
<223> OTHER INFORMATION: linked to a -C tripple bond CCH2NH2
<220> FEATURE:
<221> NAME/KEY: Misc_feature
<222> LOCATION: (6)..(6)
<223> OTHER INFORMATION: linked to a -C tripple bond CCH2NH2
<220> FEATURE:
<221> NAME/KEY: Misc_feature
<222> LOCATION: (7)..(7)
<223> OTHER INFORMATION: linked to a -C tripple bond CCH2NH2
<220> FEATURE:
<221> NAME/KEY: Misc_feature
<222> LOCATION: (8)..(8)
<223> OTHER INFORMATION: linked to a -C tripple bond CCH2NH2
<220> FEATURE:
<221> NAME/KEY: Misc_feature
<222> LOCATION: (9)..(9)
<223> OTHER INFORMATION: linked to a -C tripple bond CCH2NH2
<220> FEATURE:
<221> NAME/KEY: Misc_feature
<222> LOCATION: (10)..(10)
<223> OTHER INFORMATION: OH group at the 3' end
<220> FEATURE:
<221> NAME/KEY: Misc_feature
<222> LOCATION: (10)..(10)
<223> OTHER INFORMATION: linked to a -C tripple bond CCH2NH2

<400> SEQUENCE: 19
ctactgactg                                                          10

<210> SEQ ID NO 20
<211> LENGTH: 17
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(1)
<223> OTHER INFORMATION: linked to a -C tripple bond CCH2NH2
<220> FEATURE:
<221> NAME/KEY: Misc_feature
<222> LOCATION: (2)..(2)
<223> OTHER INFORMATION: linked to a -C tripple bond CCH2NH2
<220> FEATURE:
<221> NAME/KEY: Misc_feature
<222> LOCATION: (3)..(3)
<223> OTHER INFORMATION: linked to a -C tripple bond CCH2NH2
<220> FEATURE:
<221> NAME/KEY: Misc_feature
<222> LOCATION: (4)..(4)
<223> OTHER INFORMATION: linked to a -C tripple bond CCH2NH2
<220> FEATURE:
<221> NAME/KEY: Misc_feature
<222> LOCATION: (5)..(5)
<223> OTHER INFORMATION: linked to a -C tripple bond CCH2NH2
<220> FEATURE:
<221> NAME/KEY: Misc_feature
<222> LOCATION: (6)..(6)
<223> OTHER INFORMATION: linked to a -C tripple bond CCH2NH2
<220> FEATURE:
<221> NAME/KEY: Misc_feature
<222> LOCATION: (7)..(7)
<223> OTHER INFORMATION: linked to a -C tripple bond CCH2NH2
```

```
<220> FEATURE:
<221> NAME/KEY: Misc_feature
<222> LOCATION: (8)..(8)
<223> OTHER INFORMATION: linked to a -C tripple bond CCH2NH2
<220> FEATURE:
<221> NAME/KEY: Misc_feature
<222> LOCATION: (9)..(9)
<223> OTHER INFORMATION: linked to a -C tripple bond CCH2NH2
<220> FEATURE:
<221> NAME/KEY: Misc_feature
<222> LOCATION: (10)..(10)
<223> OTHER INFORMATION: linked to a -C tripple bond CCH2NH2
<220> FEATURE:
<221> NAME/KEY: Misc_feature
<222> LOCATION: (17)..(17)
<223> OTHER INFORMATION: OH group at the 3' end

<400> SEQUENCE: 20
ctactgactg tttttt                                                       17

<210> SEQ ID NO 21
<211> LENGTH: 17
<212> TYPE: DNA
<213> ORGANISM: Artificial Sequence
<220> FEATURE:
<223> OTHER INFORMATION: Synthetic sequence

<400> SEQUENCE: 21
ctactgactg tttttt                                                       17

<210> SEQ ID NO 22
<211> LENGTH: 17
<212> TYPE: DNA
<213> ORGANISM: Artificial Sequence
<220> FEATURE:
<223> OTHER INFORMATION: Synthetic sequence

<400> SEQUENCE: 22
tttctactga ctgtttt                                                      17

<210> SEQ ID NO 23
<211> LENGTH: 11
<212> TYPE: DNA
<213> ORGANISM: Artificial Sequence
<220> FEATURE:
<223> OTHER INFORMATION: Synthetic sequence

<400> SEQUENCE: 23
aaaaaaacta g                                                            11

<210> SEQ ID NO 24
<211> LENGTH: 17
<212> TYPE: DNA
<213> ORGANISM: Artificial Sequence
<220> FEATURE:
<223> OTHER INFORMATION: Synthetic sequence

<400> SEQUENCE: 24
aaaaaaacag tcagtag                                                      17
```